United States Patent
Macneil et al.

(10) Patent No.: US 11,426,088 B2
(45) Date of Patent: *Aug. 30, 2022

(54) SYSTEM AND METHOD TO DEFINE AN AGGREGATED STABILITY MAP OF A ROTATIONAL SOURCE OVER A PLURALITY OF TIME INTERVALS ASSOCIATED WITH A BIOLOGICAL RHYTHM DISORDER

(71) Applicant: Topera, Inc., Santa Clara, CA (US)

(72) Inventors: William Robert Macneil, Oakville, MO (US); Carey Robert Briggs, La Jolla, CA (US); Christopher Todd Schuster, St. Louis, MO (US); Heather A. Drury, Dripping Springs, TX (US)

(73) Assignee: Topera, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/999,583

(22) Filed: Aug. 21, 2020

(65) Prior Publication Data

US 2020/0375481 A1 Dec. 3, 2020

Related U.S. Application Data

(63) Continuation of application No. 15/583,593, filed on May 1, 2017, now Pat. No. 10,765,329.

(Continued)

(51) Int. Cl.
| | |
|---|---|
| *A61B 5/024* | (2006.01) |
| *G16H 50/50* | (2018.01) |
| *A61B 5/00* | (2006.01) |
| *H04W 4/35* | (2018.01) |
| *A61B 34/10* | (2016.01) |

(Continued)

(52) U.S. Cl.
CPC ........ *A61B 5/02405* (2013.01); *A61B 5/0006* (2013.01); *A61B 5/0044* (2013.01);

(Continued)

(58) Field of Classification Search
CPC ......... A61B 5/343; A61B 5/361; A61B 5/363; A61B 5/367
See application file for complete search history.

(56) References Cited

U.S. PATENT DOCUMENTS

| | | |
|---|---|---|
| 8,010,186 B1 | 8/2011 | Ryu |
| 8,715,199 B1 | 5/2014 | Macneil et al. |
| | (Continued) | |

FOREIGN PATENT DOCUMENTS

| | | |
|---|---|---|
| CN | 103458790 A | 12/2013 |
| CN | 103796576 A | 5/2014 |
| | (Continued) | |

OTHER PUBLICATIONS

International Search Report and Written Opinion issued in International Application No. PCT/US2017/030505 dated Aug. 1, 2017.

(Continued)

*Primary Examiner* — George R Evanisko
(74) *Attorney, Agent, or Firm* — Hoffmann & Baron, LLP

(57) ABSTRACT

Provided are a system and method of generating an aggregated stability map of one or more rotational sources associated with a heart rhythm disorder. In accordance therewith, a plurality of rotational area profile maps is accessed for a plurality of analysis intervals. Each of the profile maps includes rotation intensity values for a plurality of locations associated with rotation of the one or more rotational sources. An aggregated stability map is generated based on the profile maps, wherein the stability map includes a plurality of locations. Each location includes a rotation intensity value based at least on a filter number of highest rotation intensity values from corresponding locations of the profile maps, the filter number being automatically determined from a plurality of filter numbers such that the plurality of profile maps as filtered includes a predetermined (Continued)

number of rotation intensity values in excess of a threshold intensity value.

26 Claims, 14 Drawing Sheets

Related U.S. Application Data

(60) Provisional application No. 62/330,711, filed on May 2, 2016.

(51) Int. Cl.
*A61B 5/0245* (2006.01)
*H04L 67/12* (2022.01)

(52) U.S. Cl.
CPC .......... *A61B 5/0245* (2013.01); *A61B 5/6858* (2013.01); *A61B 5/744* (2013.01); *A61B 34/10* (2016.02); *G16H 50/50* (2018.01); *H04L 67/12* (2013.01); *H04W 4/35* (2018.02); *A61B 2034/105* (2016.02)

(56) References Cited

U.S. PATENT DOCUMENTS

| | | | |
|---|---|---|---|
| 10,765,329 B2 * | 9/2020 | Macneil | ................. H04L 67/12 |
| 2010/0094274 A1 | 4/2010 | Narayan et al. | |
| 2011/0251505 A1 | 10/2011 | Narayan et al. | |
| 2013/0245475 A1 | 9/2013 | Takizawa et al. | |
| 2014/0003688 A1 | 1/2014 | Hansis | |
| 2014/0088395 A1 | 3/2014 | Dubois et al. | |
| 2014/0276152 A1 * | 9/2014 | Narayan | ............ A61B 5/02405 |
| | | | 600/508 |
| 2014/0276762 A1 | 9/2014 | Parsonage | |
| 2014/0336520 A1 | 11/2014 | Zeng et al. | |
| 2014/0371616 A1 | 12/2014 | Narayan et al. | |
| 2015/0164356 A1 | 6/2015 | Merschon et al. | |
| 2015/0216435 A1 | 8/2015 | Bokan et al. | |
| 2015/0366468 A1 | 12/2015 | Levy et al. | |

FOREIGN PATENT DOCUMENTS

| | | |
|---|---|---|
| CN | 104873191 A | 9/2015 |
| CN | 105072987 A | 11/2015 |
| CN | 105361879 A | 3/2016 |
| JP | 2013-188438 A | 9/2013 |
| WO | WO 2014/030162 A1 | 2/2014 |

OTHER PUBLICATIONS

English translation of Notification of First Office Action issued in Chinese Application No. 201780027668.7 dated Nov. 2, 2020.

* cited by examiner

SYSTEM AND METHOD TO DEFINE AN AGGREGATED STABILITY MAP OF A ROTATIONAL SOURCE OVER A PLURALITY OF TIME INTERVALS ASSOCIATED WITH A BIOLOGICAL RHYTHM DISORDER

CROSS-REFERENCE TO RELATED APPLICATION

This application is a continuation of U.S. patent application Ser. No. 15/583,593, filed on May 1, 2017, which claims the benefit of and priority to U.S. Provisional Patent Application No. 62/330,711, filed on May 2, 2016, the contents of which are incorporated herein by reference in their entirety.

BACKGROUND

Field of the Disclosure

The present application relates generally to biological rhythm disorders. More specifically, the present application is directed to a system and method to define and use an aggregated stability map of a rotational source over a plurality of time intervals associated with a biological rhythm disorder, such as a heart rhythm disorder.

Brief Discussion of Related Art

Heart (cardiac) rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT), and ventricular fibrillation (VF). Other rhythm disorders, which are more simple to treat, but which may also be clinically significant, include atrial tachycardia (AT), supraventricular tachycardia (SVT), atrial flutter (AFL), supraventricular ectopic complexes/beats (SVE), and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Previously, treatment of heart rhythm disorders—particularly complex rhythm disorders of AF, VF, and polymorphic VT—has been difficult because the location in the heart that harbors the source of the heart rhythm disorder could not be identified. There have been various theories of how complex rhythm disorders function and clinical applications for treating these complex rhythm disorders. However, none of the applications proved fruitful in the treatment of complex rhythm disorders.

Recently, there has been a breakthrough discovery that identified sources associated with complex heart rhythm disorders. This technological breakthrough successfully reconstructed cardiac activation information (onset times) in signals obtained from electrodes of catheters introduced into patients' hearts to identify rotational activation patterns (rotational sources) that cause a large percentage of the heart rhythm disorders worldwide. Treatment of the heart rhythm disorders could thus be targeted to these rotational sources in the patients' hearts to eliminate the heart rhythm disorders. Such treatment could be successfully delivered by ablation, for example.

The rotational source may have one or more diffuse sections of activation that generally appear to rotate around a rotation center, but spread out diffusely about a section of the patient's heart over intervals of time. Moreover, the rotational source may have persistent or stable rotational activation that may show movement, meandering, or precessing over intervals of time. In addition, the rotational activation may further be transient over intervals of time, e.g., having persistence over some intervals of time, disappearing over one or more intervals of time, and then reappearing over other intervals of time.

Examination of activation over a plurality of intervals of time is important in obtaining a complete presentation of the rotational source associated with the heart rhythm disorder. However, a practitioner can find such examination to be time consuming and the behavior of activation over the intervals of time can be difficult to aggregate in order to understand the presentation of the rotational source of the heart rhythm disorder. While the rotational source associated with a complex heart rhythm disorder could be identified as described hereinabove, the practitioner could miss the rotational source based on the foregoing as well as other rotational behavior over multiple intervals of time, especially if the practitioner examines only one or several intervals of time out of a plurality of intervals of time associated with the heart rhythm disorder.

There are no known systems or methods to define and use an aggregated stability map of a rotational source over a plurality of time intervals associated with a biological rhythm disorder, such as a heart rhythm disorder.

SUMMARY

In accordance with an embodiment or aspect, a method of generating an aggregated stability map of one or more rotational sources associated with a heart rhythm disorder is disclosed.

The method includes accessing a plurality of rotational area profile maps generated based on sensed signals associated with the heart rhythm disorder, wherein each of the rotational area profile maps is for a respective one of a plurality of analysis intervals. Each of the rotational area profile maps includes rotation intensity values for a plurality of locations associated with rotation of the one or more rotational sources.

The method further includes filtering the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold intensity value.

Moreover, the method includes generating an aggregated stability map based on the plurality of rotational area profile maps as filtered. The aggregated stability map includes a plurality of locations, wherein each location of the plurality of locations in the aggregated stability map includes a rotation intensity value based on the highest rotation intensity values as filtered from the corresponding locations of the plurality of rotational area profile maps, wherein the rotation intensity values of the aggregated stability map help identification of and guidance to the one or more rotational sources in connection with diagnosis or treatment of the heart rhythm disorder.

The automatic determination of the filter number can include selecting a highest filter number from the plurality of filter numbers associated with the predetermined number of rotation intensity values in excess of the threshold intensity value.

The aggregated stability as generated can be presented, such as for example, on a display, wherein the aggregated stability map as generated amalgamates the rotation intensity values associated with the rotation of the one or more rotational sources over the plurality of analysis intervals.

In some embodiments or aspects, the method can also include receiving a selection of an analysis interval from the plurality of analysis intervals. An animated activation movie and a rotational area profile map can be retrieved based on the analysis interval, wherein the rotational area profile map is retrieved from the plurality of rotational area profile maps. Thereafter, the animated activation movie and the rotational area profile map overlaid over the animated activation movie can be presented, such as for example, on the display. The method can further include presenting the aggregated stability map as generated in association with the animated activation movie and the rotational area profile map.

In some embodiments or aspects, the method can include receiving a location in the aggregated stability map, wherein the location is determined from the plurality of locations in the aggregated stability map, and further determining an analysis interval related to the location, wherein the analysis interval is determined from the plurality of analysis intervals. Moreover, an animated activation movie and a rotational area profile map can be retrieved based on the analysis interval, wherein the rotational area profile map is retrieved from the plurality of rotational area profile maps, and the animated activation movie and the rotational area profile map overlaid over the animated activation movie can be presented.

In some embodiments or aspects of the method, the rotation intensity value can be a smallest rotation intensity value out of the filter number of highest rotation intensity values for that location from corresponding locations of the plurality of rotational area profile maps. The rotation intensity value can also be an average rotation intensity value of the filter number of highest rotation intensity values for that location from corresponding locations of the plurality of rotational area profile maps.

In some embodiments or aspects, the method can further include receiving a mask value, and generating the aggregated stability map with each location including the rotation intensity value based on the filter number of highest rotation intensity values from corresponding locations of the plurality of rotational area profile maps, wherein the highest rotation intensity values are masked according to the mask value.

In accordance with another embodiment or aspect, a system to generate an aggregated stability map of one or more rotational sources associated with a heart rhythm disorder is disclosed. The system includes a processor and a storage medium storing instructions that, when executed by the processor, cause the processor to perform the following operations.

The operations include accessing a plurality of rotational area profile maps generated based on sensed signals associated with the heart rhythm disorder, each of the rotational area profile maps being for a plurality of analysis intervals. Each of the rotational area profile maps includes rotation intensity values for a plurality of locations associated with rotation of the one or more rotational sources.

The operations further include filtering the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold intensity value.

Moreover, the operations include generating an aggregated stability map based on the plurality of rotational area profile maps as filtered. The aggregated stability map includes a plurality of locations, wherein each location of the plurality of locations in the aggregated stability map includes a rotation intensity value that is based on the highest rotation intensity values as filtered from the corresponding locations of the plurality of rotational area profile maps, wherein the rotation intensity values of the aggregated stability map help identification of and guidance to the one or more rotational sources in connection with diagnosis or treatment of the heart rhythm disorder.

Operations to automatically determine the filter number can include selecting a highest filter number from a plurality of filter numbers associated with the predetermined number of rotation intensity values in excess of the threshold intensity value.

The operations can further include presenting the aggregated stability map as generated, such as for example on a display, wherein the aggregated stability map as generated amalgamates the rotation intensity values associated with the rotation of the one or more rotational sources over the plurality of analysis intervals.

In some embodiments or aspects, the operations can further include receiving a selection of an analysis interval from the plurality of analysis intervals, retrieving an animated activation movie and a rotational area profile map based on the analysis interval, wherein the rotational area profile map is retrieved from the plurality of rotational area profile maps, and presenting the animated activation movie and the rotational area profile map overlaid over the animated activation movie, such as for example, on a display. Operations can further include presenting the aggregated stability map as generated in association with the animated activation movie and the rotational area profile map.

In some embodiments or aspects, the operations can further include receiving a location in the aggregated stability map, wherein the location is determined from the plurality of locations in the aggregated stability map, and further determining an analysis interval related to the location, wherein the analysis interval is determined from the plurality of analysis intervals. Operations can further include retrieving an animated activation movie and a rotational area profile map based on the analysis interval, wherein the rotational area profile map is retrieved from the plurality of rotational area profile maps, and further presenting the animated activation movie and the rotational area profile map overlaid over the animated activation movie.

In some embodiments or aspects of the system, the rotation intensity value can be a smallest rotation intensity value out of the filter number of highest rotation intensity values for that location from corresponding locations of the plurality of rotational area profile maps. The rotation intensity value can also be an average rotation intensity value of the filter number of highest rotation intensity values for that location from corresponding locations of the plurality of rotational area profile maps.

In some embodiments or aspects, the operations can further include receiving a mask value, and generating the aggregated stability map with each location including the rotation intensity value based on the filter number of highest rotation intensity values from corresponding locations of the plurality of rotational area profile maps, wherein the highest rotation intensity values are masked according to the mask value.

In accordance with a further embodiment or aspect, a method of treating a heart rhythm disorder is disclosed.

The method includes accessing a plurality of rotational area profile maps generated based on sensed signals associated with the heart rhythm disorder, each of the rotational area profile maps being for a plurality of analysis intervals. Each of the rotational area profile maps includes rotation intensity values for a plurality of locations associated with rotation of the one or more rotational sources.

The method further includes filtering the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold intensity value.

Moreover, the method includes generating an aggregated stability map based on the plurality of rotational area profile maps as filtered. The aggregated stability map includes a plurality of locations, wherein each location of the plurality of locations in the aggregated stability map includes a rotation intensity value that is based on the highest rotation intensity values as filtered from the corresponding locations of the plurality of rotational area profile maps, wherein the rotation intensity values of the aggregated stability map help identification of and guidance to the one or more rotational sources associated with the heart rhythm disorder.

In some embodiments or aspects of the method, the aggregated stability map as generated can be presented, such as for example, on a display, wherein the aggregated stability map amalgamates the rotation intensity values associated with the rotation of the one or more rotational sources over the plurality of analysis intervals.

In some embodiments or aspects of the method, the rotation intensity value can be a smallest rotation intensity value out of the filter number of highest rotation intensity values for that location from corresponding locations of the plurality of rotational area profile maps. The rotation intensity value can also be an average rotation intensity value of the filter number of highest rotation intensity values for that location from corresponding locations of the plurality of rotational area profile maps.

In some embodiments or aspects, the method can further include receiving a mask value, and generating the aggregated stability map with each location including the rotation intensity value based on the filter level of highest rotation intensity values from corresponding locations of the plurality of rotational area profile maps, wherein the highest rotation intensity values are masked according to the mask value.

In some embodiment or aspects, the one or more locations can form a cluster.

The method further includes treating the heart rhythm disorder at a rotational source of the one or more rotational sources based on one or more locations of the aggregated stability map having a rotation intensity value in excess of the threshold rotational intensity value. For example, a cluster having locations in excess of the threshold rotational intensity value can be treated. Treatment can be delivered to heart tissue at the locations and can include ablation, for example. Other treatments of the heart tissue are of course possible, e.g., various energy sources (including but not limited to radiofrequency, cryoenergy, microwave, and ultrasound), gene therapy, stem cell therapy, pacing stimulation, drug or other therapy.

These and other purposes, goals, and advantages of the present application will become apparent from the following detailed description read in connection with the accompanying drawings.

BRIEF DESCRIPTION OF THE DRAWINGS

Some embodiments or aspects are illustrated by way of example and not limitation in the figures of the accompanying drawings in which.

DETAILED DESCRIPTION

A system and method to define an aggregated stability map of a rotational source over a plurality of time intervals are disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

Figure 1:
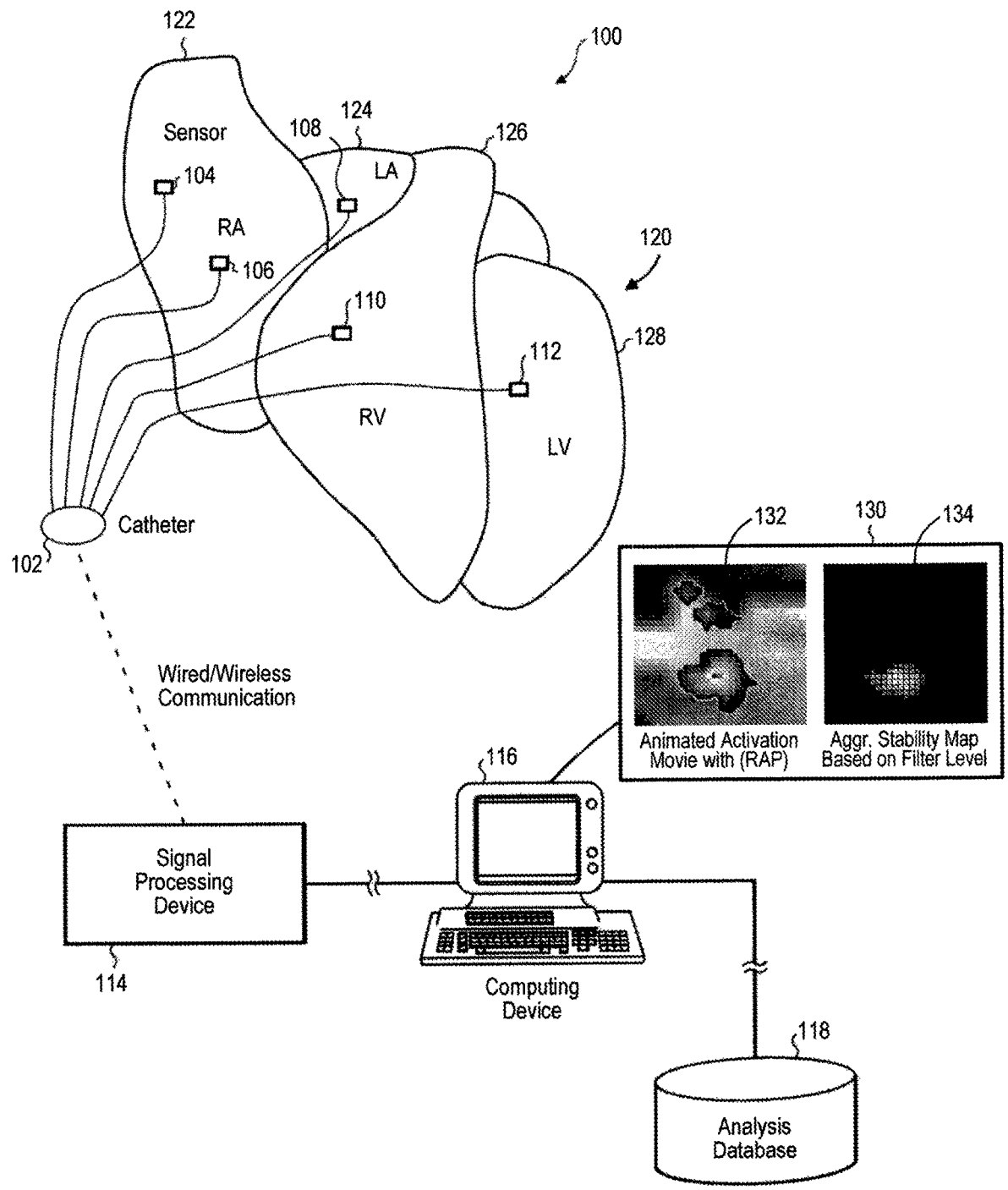
FIG. 1 illustrates an example system capable of defining an aggregated stability map of a rotational source over a plurality of time intervals, the rotational source associated with a heart rhythm disorder.

FIG. 1 illustrates an example system 100 capable of defining an aggregated stability map of a rotational source over a plurality of time intervals, the rotational source being associated with a heart rhythm disorder of a patient's heart 120.

More specifically, the example system 100 is configured to identify the rotational source over a plurality of time intervals, and further configured to amalgamate or aggregate rotational information associated with the rotational source over the time intervals into the aggregated stability map associated with the heart rhythm disorder. The aggregated stability map can help a practitioner to better understand the rotational behavior of the source over the plurality of time intervals, and accordingly to deliver more precise treatment to the source of the heart rhythm disorder.

As particularly illustrated in FIG. 1, the heart 120 includes a right atrium 122, left atrium 124, right ventricle 126, and left ventricle 128. The example system 100 includes a basket catheter 102, signal processing device 114, computing device 116, and analysis database 118. The catheter 102 can detect cardiac electrical information in the heart 120 and can transmit the detected cardiac electrical information to the signal processing device 114, either via a wireless or wired connection. The catheter 102 includes a plurality of sensors 104-112, which can be inserted into the heart 120 through the patient's blood vessels.

In some embodiments or aspects, one or more of the sensors 104-112 are not inserted into the patient's heart 120. For example, some sensors can detect cardiac electrical information via the patient's surface (e.g., electrocardiogram) or remotely without contact with the patient (e.g., magnetocardiogram or methods to identify electrical information via the inverse solution). As another example, some sensors may also derive cardiac electrical information from cardiac motion of a non-electrical sensing device (e.g., echocardiogram). In various embodiments or aspects, the foregoing sensors can be used separately or in different combinations, and further the separate or different combinations can also be used in combination with sensors that are inserted into the patient's heart 120.

The sensors 104-112 are positioned at respective sensor locations in respect to the heart 120, e.g., adjacent to or contacting tissue in the heart 120 or near the heart 120. The sensors 104-112 can detect cardiac electrical information at the sensor locations and can generate corresponding sensed signals which are output to the signal processing device 114. The sensors 104-112 can further deliver energy to ablate the heart 120 at the sensor locations, particularly when the sensor location is adjacent to or contacting the tissue in the heart 120.

The signal processing device 114 can process (e.g., clarify and amplify) sensed signals generated by the sensors 104-112 and can further output corresponding cardiac signals to the computing device 116. There can be 64, 128, or another number of cardiac signals output by signal processing device 114. The computing device 116 receives or accesses the cardiac signals for analysis and processing in accordance with methods disclosed herein. For example, the computing device 116 can receive or access the cardiac signals from the signal processing device 114. Alternatively, the cardiac signals can be stored in the analysis database 118, and the computing device 116 can receive or access the cardiac signals from the analysis database 118.

The computing device 116 can process the cardiac signals in order to identify rotational information associated with the rotational source over a plurality of time intervals. The computing device 116 can further amalgamate the rotational information over these time intervals into an aggregated stability map associated with the heart rhythm disorder. More specifically, the computing device 116 can generate a graphical user interface (GUI) 130 that presents an animated activation movie with a rotational area profile (RAP) 132 for a certain time interval, as well as an aggregated stability map 134, which amalgamates rotational information over a plurality of time intervals that is associated with a rotational source of a heart rhythm disorder. As will be described in greater detail hereinbelow, the aggregated stability map 134 can be based on filtering the rotational information according to filter level (L). In some cases, the rotational information that is filtered can be averaged, or averaged and rounded. In addition, the aggregated stability map 134 can be based on filtering the rotational information according to filter level (L) and a rotational intensity threshold mask value (Q). In some other cases, the aggregated stability map 134 can be based on averaging the rotational information over these time intervals.

For example, the computing device 116 can generate animated activation movies for various intervals of time using monophasic action potential maps (MAPs) associated with one or more sources of a heart rhythm disorder, as described in U.S. Pat. No. 8,165,666, which is incorporated herein by reference in its entirety. In particular, FIG. 11 of the '666 patent illustrates an animated activation movie of constituent MAPs for a certain interval of time showing a source of a heart rhythm disorder. Similarly, other systems and methods that can generate animated activation movies for various intervals of time associated with one or more sources of a heart rhythm disorder can be used.

As another example, the computing device 116 can further generate RAPs for the respective animated activation movies using heat maps, as described in U.S. Pat. No. 9,332,915 granted on May 10, 2016, which is incorporated herein by reference in its entirety. In particular, FIG. 9 of the '915 patent illustrates overlaying or superimposing a heat map over an animated activation movie, which depicts intensity of rotational information during the animated activation movie. Similarly, other systems and methods that can generate RAPs for the respective animated activation movies can be used.

The aggregated stability map 134 can amalgamate rotational information over a plurality of time intervals in various approaches, which can assist a practitioner to better understand the rotational behavior of the rotational source over the plurality of time intervals, and accordingly guide the practitioner to the source of the heart rhythm disorder in order to deliver more precise treatment (e.g., more focused and/or targeted treatment) to the rotational source of the heart rhythm disorder. In particular, FIGS. 2-11 illustrate various examples of generating the aggregated stability map 134 based on the RAPs associated with the respective animated activation movies over the plurality of time intervals.

Figure 2:
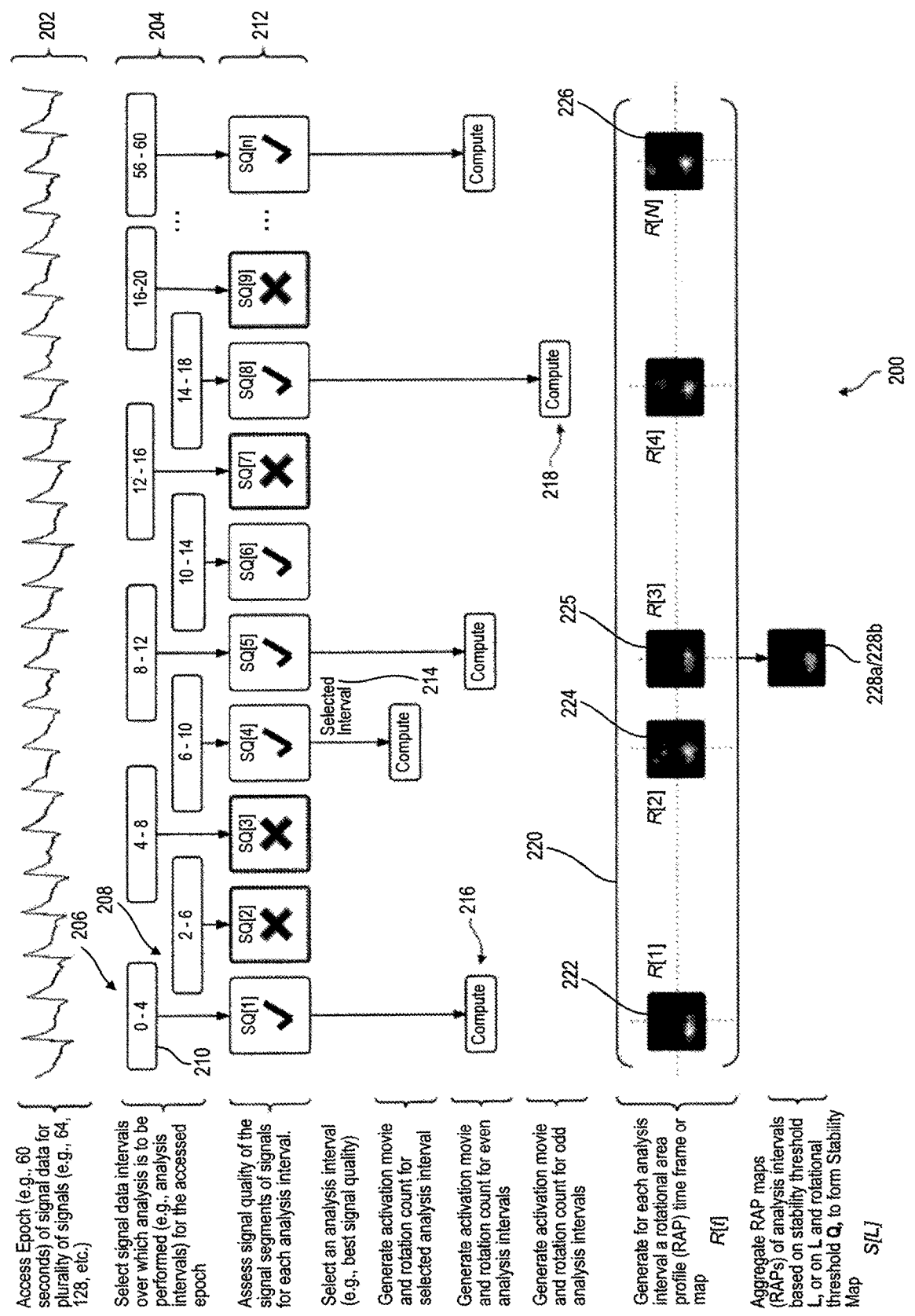
FIG. 2 illustrates an example block diagram of rotational area profile (RAP) maps amalgamated over a plurality of analysis intervals into an aggregated stability map based on a threshold filter level.

FIG. 2 illustrates an example block diagram 200 that shows amalgamation of RAPs over a plurality of time (analysis) intervals into an aggregated stability map 228a based on a threshold filter level (L), or an aggregated stability map 228b based on a filter level (L) and a rotational intensity threshold mask value (Q). As will be described in greater detail hereinbelow, other approaches can be used to amalgamate the RAPs over a plurality of time (analysis) intervals into an aggregated stability map.

As illustrated in the block diagram at 202, an epoch (e.g., 60 seconds) of signal data for a plurality of cardiac signals can be accessed. The epoch of signal data can include 64, 128, or another number of cardiac signals. As illustrated at 204, a selection is made as to the time (analysis) intervals over which the analysis is to be performed. For example, each of the analysis intervals can be four (4) seconds in length, such as fifteen (15) even intervals 206 (e.g., 0-4, 4-8, 8-12, . . . , 56-60) and also fourteen (14) odd intervals 208 (e.g., 2-6, 6-10, 10-14, . . . , 54-58). The odd intervals can overlap the adjacent even intervals. As an example, a total of twenty-nine (29) analysis intervals can be defined for the 60-second epoch of signal data.

Moreover, the signal data of a signal for a certain analysis interval can be considered as a signal segment. Signal segments of the cardiac signals during each analysis interval can be assessed for signal quality, for example, as described in U.S. patent application Ser. No. 14/483,914, filed on Sep. 11, 2014, granted as U.S. Pat. No. 10,368,764 on Aug. 6, 2019. Similarly, other systems and methods that can assess signal quality of signal segments of the cardiac signals during each analysis interval can be used.

For example, during the first analysis interval 210, signal segments (e.g., 64, 128, or more signal segments) for corresponding cardiac signals (e.g., 64, 128, or more signals) during the first analysis interval 210 (e.g., 0-4 seconds) can be assessed for signal quality.

Figure 9:
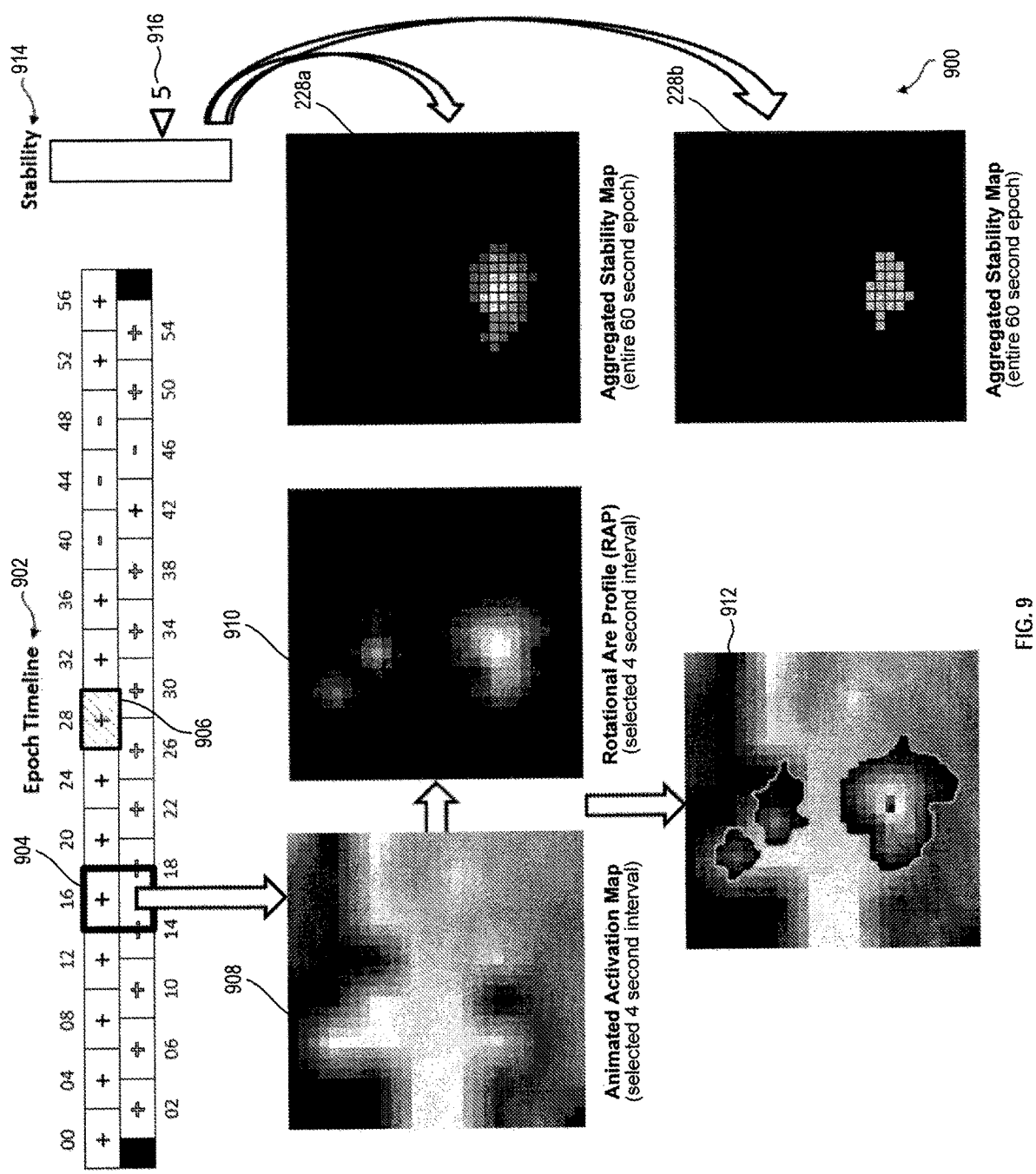
FIG. 9 illustrates an example graphical user interface generated in accordance with FIGS. 1-8.
Figure 10:
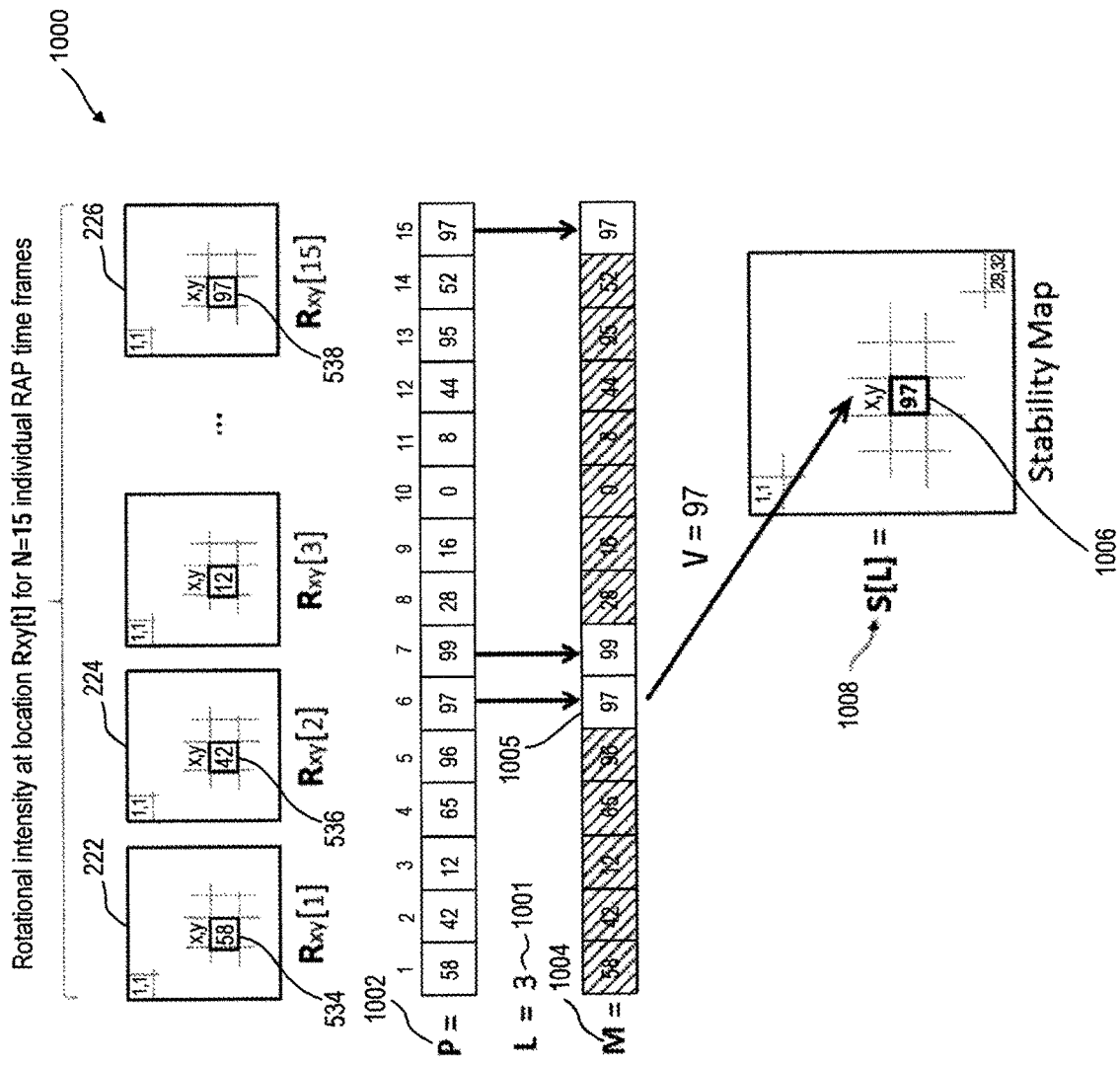
FIG. 10 illustrates a block diagram of an aggregated stability map generated based on an adjusted filter level from RAP maps as described in connection with FIG. 5A.

In particular, FIG. 9 of the '764 patent illustrates a computation of maximum autocorrelation coefficients for the signal segments of an analysis interval, and FIG. 10 illustrates computation of a composite correlation coefficient (e.g., sum, mean, etc.) of the individual autocorrelation coefficients of the signal segments for the analysis interval. Acceptable signal quality can be determined when the composite correlation coefficient is assessed to be in excess of a predetermined threshold (e.g., 0.5) and is indicated in FIG. 2 of the present application as a checkmark. In contrast, signal quality that is not acceptable is indicated in FIG. 2 as an x-mark.

In addition, the composite correlation coefficients of the plurality of analysis intervals can also be assessed for best signal quality. For example, the analysis interval 214 (e.g., 6-10 second interval) having the best signal quality among the plurality of analysis intervals can be selected.

As further illustrated in FIG. 2, animated activation movies and rotational information (e.g., rotation counts) are generated for the odd analysis intervals and the even analysis intervals that are acceptable, as illustrated at 216 and 218. Moreover, as illustrated at 220 a rotational area profile (RAP) map is generated based on rotational information for each analysis interval that is assessed to have acceptable signal quality. For example, RAPs 222, 224, . . . , and 226 are generated for the corresponding analysis intervals. Thereafter, the generated RAPs are amalgamated into an aggregated stability map 228a or an aggregated stability map 228b based on a filter level (L), or a filter level (L) and a rotational intensity threshold mask value (Q), or one or more other approaches, as will be described in greater detail hereinbelow.

Figure 3:
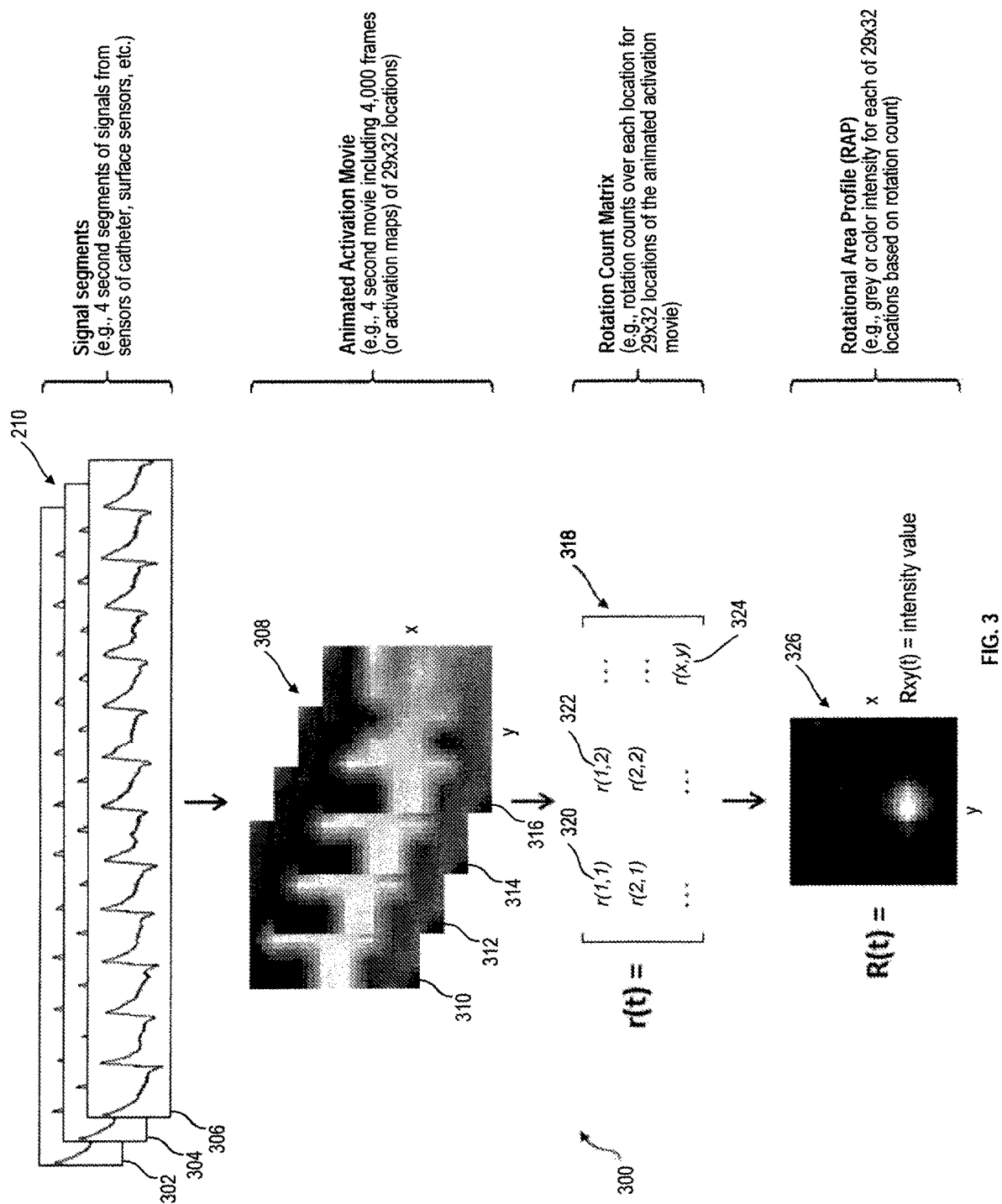
FIG. 3 illustrates an example block diagram of an example RAP map generated for signal segments of an acceptable analysis interval.

FIG. 3 illustrates an example block diagram 300 showing an example RAP map 326 generated for signal segments 302-306 of an acceptable interval of time (analysis interval) 210. As described hereinabove, four-second signal segments (e.g., 64, 128, or other number of segments) of the corresponding cardiac signals (e.g., 64, 128, or other number of cardiac signals) for time interval 210 are used to generate a four-second animated activation movie 308.

The animated activation movie 308 includes a plurality of activation maps, e.g., activation maps 310-316 are representative. It is noted that the four-second activation movie 308 generally includes 4,000 activation maps, one map for each millisecond of the activation movie 308. Each of the activation maps generally includes 29×32 x-y locations on a Cartesian grid. A rotation count matrix (r(t)) 318 is generated for the animated activation movie 308. More specifically, matrix(t) 318 includes a rotation count for each x-y location across the frames (4,000) of the animated activation movie 308.

As an example, the rotation count in the '915 patent is determined for each area as defined on a spline-sensor grid (A-H splines×1-8 sensors). For purposes of interpolation between the spline-sensor grid and the Cartesian grid, a center location of each area can be considered in connection with the rotation count determined for that area. Accordingly, the spline-sensor grid can be transformed to the Cartesian grid having 29-32 x-y locations by adding three (3) x-y locations between the sensors bounding each area. Because the splines A-H wrap around the basket catheter 102, an extra three (3) x-y locations are used between sensors along the A to H splines, for a total of 29×32 x-y locations. The rotation counts for the x-y locations are then linearly interpolated based on rotation counts of the center locations between which the x-y locations are added, the locations 320, 322, . . . , and 324 being representative.

Thereafter, a rotational area profile (RAP) map (R(t)) 326 is generated based on the rotation count matrix. More specifically, the RAP map generally includes 29×32 x-y locations on a Cartesian grid. Each x-y location is assigned a color or greyscale intensity value based on the rotation count determined from the 4,000 frames of animated activation movie 308. For example, black can be zero (0) rotation count out of 4,000 frames, blue can be three-hundred (300) rotation count out of 4,000 frames, green can be six-hundred (600) rotation count out of 4,000 frames, yellow can be a nine-hundred (900) rotation count out of 4,000 frames, and red can be a twelve-hundred (1,200) rotation count out of 4,000 frames.

The color or greyscale $R_{xy}(t)$ intensity values depend on actual rotation count as determined. It should be noted that different rotation count-color intensity ranges can be defined. Similarly, as shown in FIG. 3 the greyscale intensity levels are defined based on the foregoing ranges of rotation counts, e.g., zero (0) rotation count can be black, 1,200 rotation count can be white, while the other ranges are determined between these greyscale intensities. Similarly, different rotation count-greyscale intensity ranges can be defined.

Figure 4:
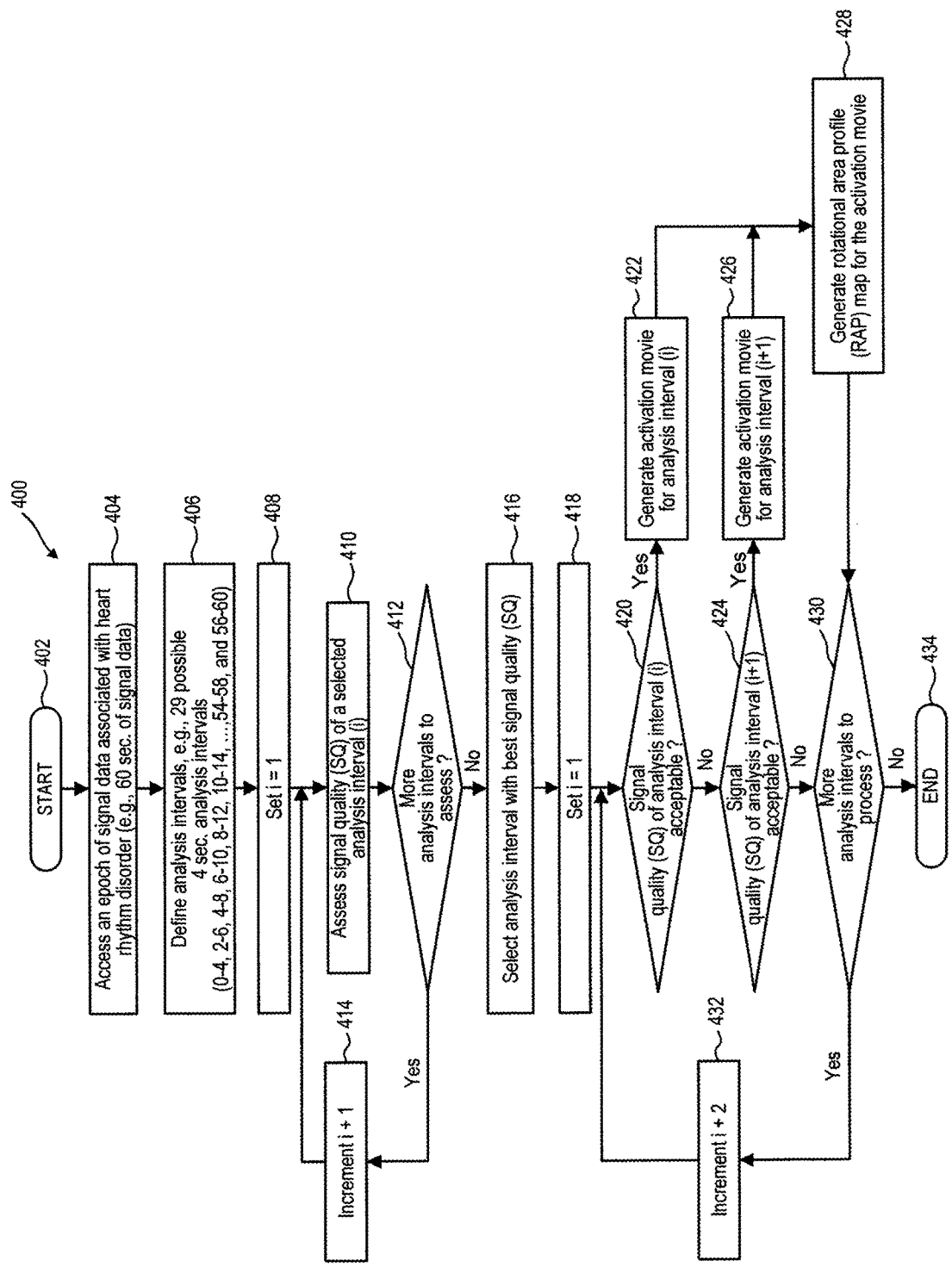
FIG. 4 illustrates a flowchart of an example method of generating RAP maps from animated activation movies associated with the analysis intervals based on signal quality.

FIG. 4 is a flowchart of an example method 400 that generates rotational area profile (RAP) maps from the animated activation movies associated with the analysis time intervals based on signal quality.

The method 400 starts at operation 402, where the signal processing device 114 has processed a plurality of signals (e.g., 64, 128, or another number of signals) of an epoch (e.g., 60 seconds of signal data) and has generated corresponding cardiac signals. As described hereinabove, the signal processing device 114 can provide the cardiac signals to the computing device 116 or can store the cardiac signals in the analysis database 118. It is noted that the epoch can be defined to include a different length of signal data obtained from a patient (e.g., 30 seconds, 90 seconds, or another length of signal data).

At operation 404, the epoch of signal data is accessed by computing device 116 from the processing device 114 or from the analysis database 118. The signal data is obtained from a patient and relates to a complex heart rhythm disorder (e.g., AF, VF, polymorphic VT, etc.), which harbors a rotational source associated with the heart rhythm disorder.

At operation 406, a plurality of analysis intervals are defined for the signal data of the epoch. More specifically, each of the analysis intervals can be four (4) seconds in length, such as fifteen (15) even intervals (e.g., 0-4, 4-8, 8-12, . . . , 56-60) and also fourteen (14) odd intervals (e.g., 2-6, 6-10, 10-14, . . . , 54-58). A total of twenty-nine (29) intervals can be defined for the 60 seconds of signal data. A different number of analysis intervals can be defined, e.g., two-second lengths (e.g., even intervals 0-2, 2-4, . . . , and 58-60, and odd intervals 1-3, 3-5, . . . , and 57-59).

At operation 408, an index (i) is set to the first analysis interval (e.g., i=1) of signal data. At operation 410 the signal quality (sq) of signal segments from cardiac signals for the analysis interval (i) is assessed. For example, assessment can include determination of autocorrelation coefficients for the signal segments of the analysis interval (i), and a determination of a composite correlation coefficient based on the individual autocorrelation coefficients of the signal segments. At operation 412, a determination is made as to whether there are more analysis intervals to process. If it is determined at operation 412 that there are more analysis intervals to assess, the method 400 continues at operation 414, where the index (i) is incremented to the next analysis interval (e.g., i+1). Thereafter, operations 410-414 are performed to assess further analysis intervals of the epoch of signal data.

However, if it is determined at operation 412 that there is no further analysis interval to assess at operation 412, the method 400 continues at operation 416 that selects an analysis interval with best signal quality from the plurality of analysis intervals. For example, the analysis interval associated with the highest composite correlation coefficient can be selected.

At operation 418, an index (i) is again set to the first analysis interval (e.g., i=1). At operation 420, a determination is made as to whether the signal quality (sq) of an even analysis interval (i) is acceptable. Determination of whether signal quality is acceptable can be made based on whether the composite correlation coefficient is in excess of a pre-determined threshold. If it is determined at operation 420 that the signal quality (sq) of the even analysis interval (i) is acceptable, the method 400 continues at operation 422, where an animated activation movie is generated based on the signal segments from cardiac signals for the even analysis interval (i). Thereafter, the method 400 continues at operation 428, which is described in greater detail hereinbelow.

However, if it is determined at operation 420 that the signal quality (sq) of the even analysis interval (i) is not acceptable, the method 400 continues at operation 424, where a further determination is made as to whether signal quality (sq) of the odd analysis interval (i+1) is acceptable. Acceptability of signal quality can be determined as already described hereinabove. If it is determined at operation 424 that the signal quality (sq) of the odd analysis interval (i+1) is acceptable, the method 400 continues at operation 426, where an animated activation movie is generated based on the signal segments from cardiac signals for the odd analysis interval (i+1). Thereafter, the method 400 continues at operation 428, where a rotation area profile (RAP) map is generated for the animated activation movie resultant from either the even analysis interval of operation 422 or the odd analysis interval of operation 426. Thereafter, the method 400 continues at operation 430 described hereinbelow.

However, if it is determined at operation 424 that the signal quality (sq) of the odd analysis interval (i+1) is not acceptable, the method 400 continues at operation 430, where a determination is made as to whether there are more analysis intervals to process. If it is determined at operation 430 that there are more analysis intervals to process, the method 400 continues at operation 432, where the index (i) is incremented to the next even analysis interval (e.g., i+2). Thereafter, operations 420-430 are performed to process further analysis intervals of the epoch of signal data, generating for each processed analysis interval an animated activation movie and a corresponding RAP.

However, if it is determined at operation 430 that there is more analysis interval to process, the method 400 ends at operation 434. Accordingly, for each processed analysis interval having acceptable signal quality (sq) there have been generated an animated activation movie and a corresponding RAP. It is noted that the animated activation movies and corresponding RAPs for the processed analysis intervals can be stored in the analysis database 118.

Figure 5A:
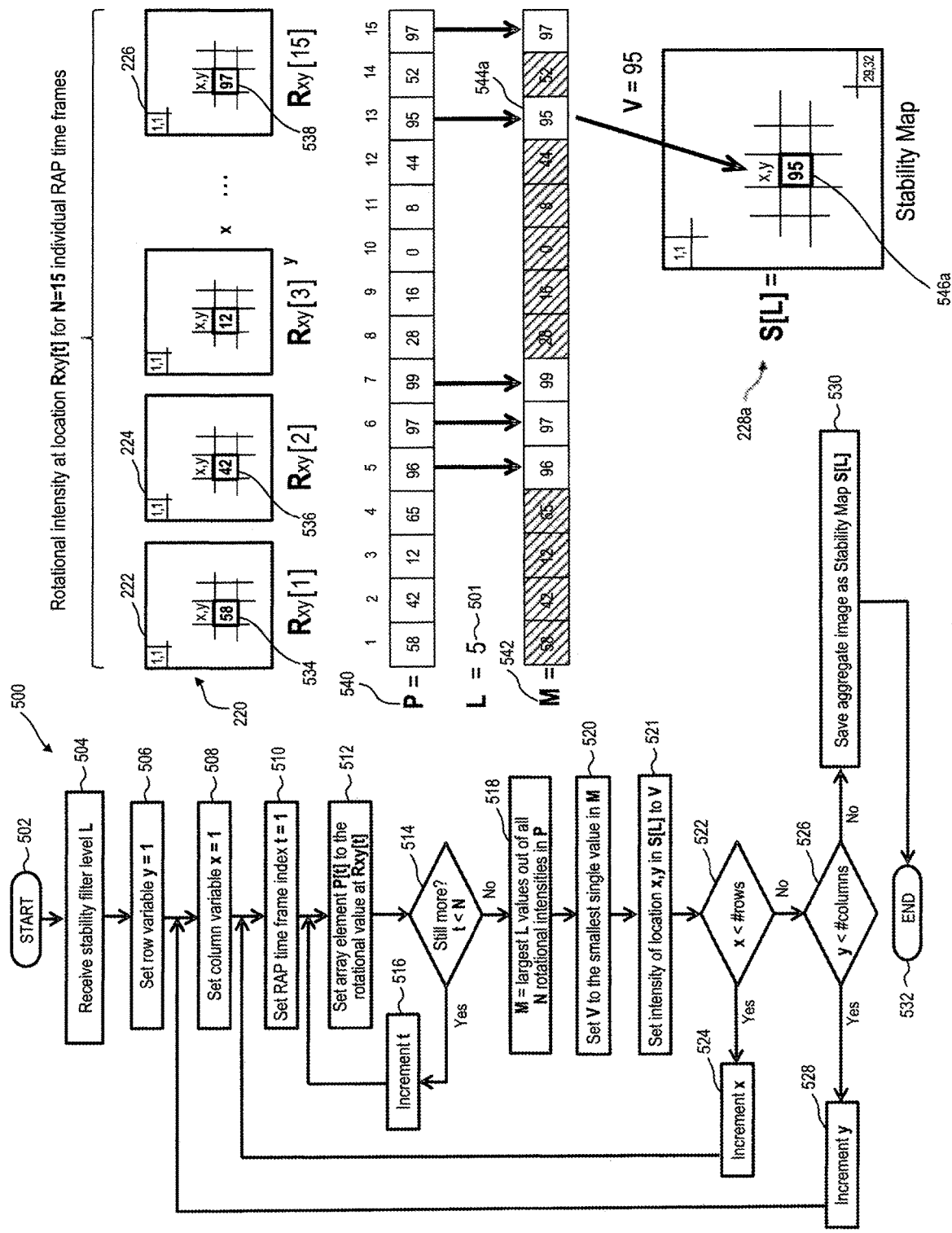
FIG. 5A illustrates a flowchart of an example method of generating an aggregated stability map from RAP maps based on a filter level.

FIG. 5A is a flowchart of an example method 500 that generates an aggregated stability map based on a filter level (L), from rotational area profile (RAP) maps or RAPs. In this example, L equals to five (L=5).

The method 500 starts at operation 502, where RAPs are accessed for N-analysis intervals or time-frames (e.g., fifteen (15) analysis intervals were processed). For example, the RAPs can be accessed from the analysis database 118. As described previously, a RAP for an interval of time (t) includes intensity values for 29×32 locations, as illustrated for example by R(t) 326 in FIG. 3.

At operation 504, a stability filter level (L) is received. The filter level (L) can be determined programmatically (e.g., initial filter level), and further can also be provided by a practitioner. For example, an example filter level 501 (L=5) can be determined programmatically as described with reference to FIG. 6, or can be provided using a stability level selector as described with reference to FIG. 9.

At operations 506 and 508, indices x and y are set to a first x-y location (e.g., x=1 and y=1) to be processed in a certain RAP map. At operation 510, a time-frame index is set to a certain RAP (e.g., t=1 for a first RAP) out of N-number of time frames (e.g., N=15 for fifteen time frames associated with fifteen RAPs). An array P 540 is defined to include N-number of elements for an x-y location across the N-number of RAPs (e.g., 534, 536, . . . , and 538 across N-number of RAPs 222, 224, . . . , and 226 for a certain x, y location). Thereafter, at operation 512 an array element P[t] (e.g., P[1]) is set to the rotational intensity value Rxy[t] (e.g., Rxy[1]=58, intensity value of x-y location 534). At operation 514, a determination is made as to whether there are more time-frames to process (e.g., is time frame t<N-number of time frames). If it is determined at operation 514 that there are more time frames to process, the method 500 continues at operation 516, where t is incremented to the next time frame (e.g., t+1). Operations 512-514 are performed to process successive time frames t, setting successive array elements of the array P[t] to the intensity values for location x-y across the N-number of RAPs.

However, if it is determined at operation 514 that there are no more time frames to process, the method 500 continues at operation 518 to define an array M 542, which includes largest L-number of intensity values from the N-intensity values in the P array 540. For example, for filter level L=5, M array 542 is defined to include the largest five (5) intensity values out of the fifteen intensity values in the P array 540 (e.g., intensity values 96, 97, 99, 95, and 97 for certain x-y location across N-number of RAPs 222, 224, . . . , and 226). At operation 520, an intensity value V is set to the smallest intensity value 544a out of the intensity values included in the M array (e.g., value V=95 for certain x-y location across N-number of RAPs 222, 224, . . . , and 226). Thereafter, at operation 521 the aggregated stability map 228a for the filter level L=5 is generated by setting location (x, y) 546a in aggregated stability map S[L] to V (e.g., value for location (x, y) 546a is set to 95).

In some cases, the intensity value V can be set to an average intensity value out of the largest intensity values included in the M array. If so, then at operation 520 the intensity value V is set to the average value of the largest intensity values in the M array (e.g., value V=96.8 for certain x-y location across N-number of RAPs 222, 224, . . . , and 226). This value can be rounded to a nearest whole value (e.g., V=97). Thereafter, at operation 521 the aggregated stability map 228a for the filter level L=5 is generated by setting location (x, y) 546a in aggregated stability map S[L] to V (e.g., value for location (x, y) 546a is set to value 96.8 or rounded value 97). The foregoing can help to provide better contrast continuity of rotational intensity values for the different x-y locations of the stability map S(L) based on the averaged rotational intensity values of the M arrays for the different x-y locations in the stability map 228a.

At operation 522, a determination is made as to whether there are more rows to process. If it is determined at operation 522 that there are more rows to process, index x is incremented (e.g., x+1) at operation 524, and the method 500 continues again at operation 510. Operations 510-522 are performed to process an x-y intensity value for all rows across the N-number of RAPs. However, if it is determined at operation 522 that there are no more rows to process, the method 500 continues at operation 526, where a determination is made as to whether there are more columns to process. If it is determined at operation 526 that there are more columns to process, index y is incremented (e.g., y+1) at operation 528, and the method 500 continues again at operation 508. Operations 508-526 are performed to process an x-y intensity value for all columns across the N-number of RAPs.

However, if it is determined at operation 526 that there are no more columns to process, the method 500 continues at operation 530, where a completed aggregated stability map S[L] is saved. For example, the aggregated stability map S[L] can be saved to the analysis database 118. It should be noted that the example method 500 sets 29×32 x-y locations in the aggregated stability map 228a based on filter level L (e.g., S[L]), in accordance with the description provided hereinabove.

Figure 5B:
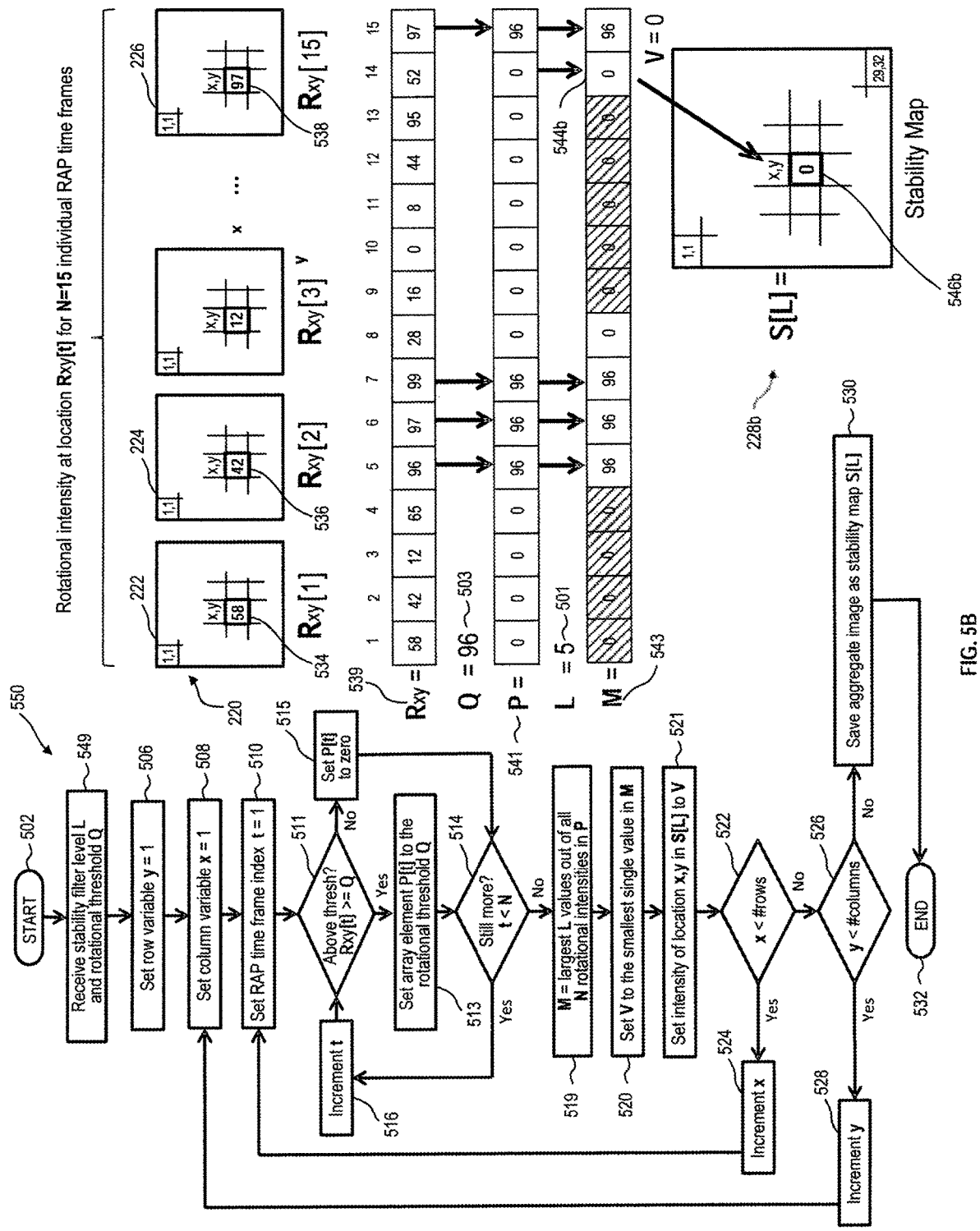
FIG. 5B illustrates a flowchart of an example method of generating an aggregated stability map from RAP maps based on a filter level and a rotational intensity threshold mask value.

FIG. 5B is a flowchart of an example method 550 that generates an aggregated stability map based on a filter level (L) and a rotational intensity threshold mask value (Q), from rotational area profile (RAP) maps or RAPs. The method 550 is similar to method 500, except that a mask value (Q) is received in addition to a stability filter level (L). The mask value (Q) is to be applied to the RAPs and forms an intensity threshold mask that is applied to the rotational intensity values across N-number of RAPs, as will be described in greater detail hereinbelow. In the example that follows L is equal to five (L=5) and Q is equal to a mask value of 96 (Q=96). It is noted that other mask values can be used.

The method 550 starts at operation 502, where RAPs are accessed for N-analysis intervals or time-frames (e.g., fifteen (15) analysis intervals were processed). For example, the RAPs can be accessed from the analysis database 118. As described previously, a RAP for an interval of time (t) includes intensity values for 29×32 locations, as illustrated for example by R(t) 326 in FIG. 3.

At operation 549, a stability filter level (L) and a mask value (Q) are received. The filter level (L) can be determined programmatically (e.g., initial filter level), and further can also be provided by a practitioner. An example filter level 501 (L=5) can be determined programmatically as described with reference to FIG. 6, or can be provided using a stability level selector as described with reference to FIG. 9. Similarly, the mask value (Q) can be determined programmatically, can be provided by a practitioner, and/or can further be a predetermined mask value.

In some embodiments or aspects, the mask value Q can be determined programmatically by applying statistical principles to the raw Rxy values of the RAPs in order to determine a meaningful threshold indicative of intensity peaks. For example, a mean of the Rxy values can be computed and one (1) or two (2) standard deviations can then be added to the mean to determine the mask value Q. Other established statistical methods could similarly be used to calculate such a mask value Q in order to bring prominence to the intensity peaks in the raw Rxy values of the RAPs.

At operations 506 and 508, indices x and y are set to a first x-y location (e.g., x=1 and y=1) to be processed in a certain RAP map. At operation 510, a time-frame index is set to a certain RAP (e.g., t=1 for first RAP) out of N-number of time frames (e.g., N=15 for fifteen time frames associated with fifteen RAPs). An array Rxy 539 is defined to include N-number of elements for an x-y location across the N-number of RAPs (e.g., 534, 536, . . . , and 538 across N-number of RAPs 222, 224, . . . , and 226 for a certain x, y location). Moreover, a mask array P 541 is defined and includes N-number of elements that are associated with the respective elements of the array Rxy 539.

Thereafter, at operation 511 a determination is made as to whether a selected array element Rxy[t] of the array Rxy 539 is greater than or equal to the mask value (Q) (Rxy[t]>=Q). If it is determined at operation 511 that the selected array element is greater than or equal to the mask value (Q), the method 550 continues at operation 513 where the associated array element P[t] in the mask array P 541 is set to the rotational intensity value indicated by the mask value (Q) (e.g., Rxy[5]=96). However, if it is determined at operation 511 that the selected array element Rxy[t] of the array Rxy 539 is not greater than or equal to the mask threshold value (Q), the method 550 continues at operation 515 where the associated array element P[t] of the mask array P 541 is set to the rotational intensity value of zero (0) (e.g., Rxy[1]=0).

A determination is made at operation 514 as to whether there are more time-frames to process (e.g., is time frame t<N-number of time frames). If it is determined at operation 514 that there are more time frames to process, the method 550 continues at operation 516, where t is incremented to the next time frame (e.g., t+1). Operations 511-516 are performed to process successive time frames t, setting successive array elements of the array P[t] to the rotational intensity indicated by the mask value (Q) or zero (0) across the N-number of RAPs.

However, if it is determined at operation 514 that there are no more time frames to process, the method 550 continues at operation 519 to define an array M 543, which includes largest L-number of intensity values as masked according to mask value (Q) from the N-intensity values in the P array 541. For example, for filter level L=5 and Q=96, M array 543 is defined to include the largest five (5) intensity values as masked by Q out of the fifteen intensity values in the P array 541 (e.g., intensity values 96, 96, 96, 0, and 96 associated with certain x-y location across N-number of RAPs 222, 224, . . . , and 226). At operation 520, an intensity value V is set to the smallest intensity value 544b out of the intensity values as masked according to (Q) included in the M array (e.g., value V=0 for certain x-y location across N-number of RAPs 222, 224, . . . , and 226). Thereafter, at operation 521 the aggregated stability map 228b for the filter level L=5 and mask value Q=96 is generated by setting location (x, y) 548 in aggregated stability map S[L] to value V (e.g., value for location (x, y) 546b is set to zero (0)).

At operation, 522, a determination is made as to whether there are more rows to process. If it is determined at operation 522 that there are more rows to process, index x is incremented (e.g., x+1) at operation 524, and the method 550 continues again at operation 510. Operations 510-522 are performed to process an x-y intensity value as masked by Q for all rows across the N-number of RAPs. However, if it is determined at operation 522 that there are no more rows to process, the method 550 continues at operation 526, where a determination is made as to whether there are more columns to process. If it is determined at operation 526 that there are more columns to process, index y is incremented (e.g., y+1) at operation 528, and the method 550 continues again at operation 508. Operations 508-526 are performed to process an x-y intensity value as masked by Q for all columns across the N-number of RAPs.

However, if it is determined at operation 526 that there are no more columns to process, the method 550 continues at operation 530, where a completed aggregated stability map S[L] 228b is saved. For example, the aggregated stability map S[L] 228b can be saved to the analysis database 118. It should be noted that the example method 550 sets 29×32 x-y locations in the aggregated stability map based on filter level (L) as masked by mask value (Q), in accordance with the description provided hereinabove.

Figure 5C:
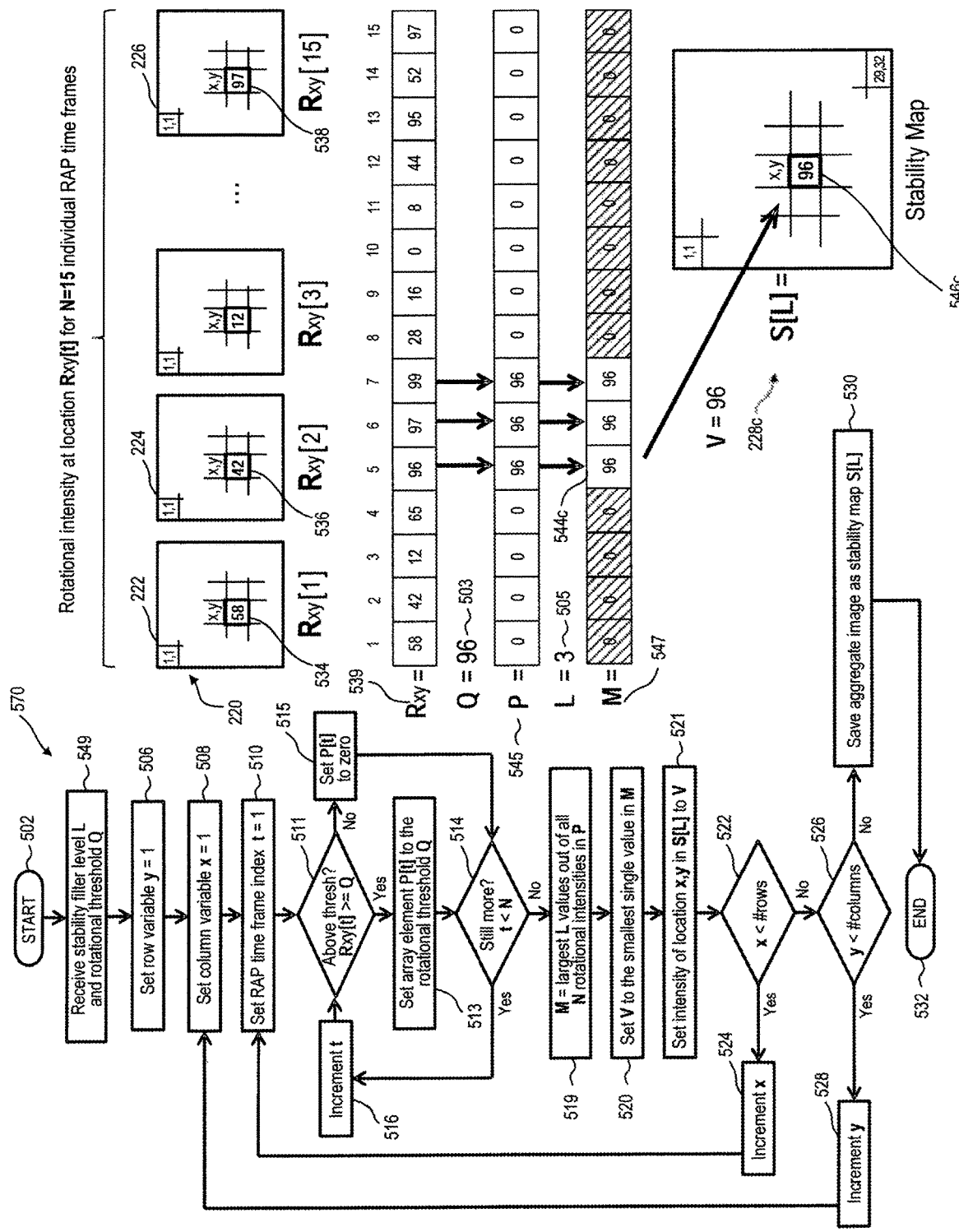
FIG. 5C illustrates a flowchart of another example method of generating an aggregated stability map from RAP maps based on another filter level and another rotational intensity threshold mask value.

FIG. 5C is a flowchart of an example method 570 that generates an aggregated stability map based on another filter level (L) and another rotational intensity threshold mask value (Q), from rotational area profile (RAP) maps or RAPs. The method 570 is similar to method 550, except for the received stability filter level (L) and array M as generated based on the stability filter level (L) and mask value (Q). In the example that follows L is equal to three (L=3) and Q is equal to a mask value of 96 (Q=96).

The method 570 starts at operation 502, where RAPs are accessed for N-analysis intervals or time-frames (e.g., fifteen (15) analysis intervals were processed). For example, the RAPs can be accessed from the analysis database 118. As described previously, a RAP for an interval of time (t) includes intensity values for 29×32 locations, as illustrated for example by R(t) 326 in FIG. 3.

At operation 549, a stability filter level (L) and a mask threshold value (Q) are received. The filter level (L) can be determined programmatically (e.g., initial filter level), and further can also be provided by a practitioner. An example filter level 503 (L=3) can be determined programmatically as described with reference to FIG. 6, or can be provided using a stability level selector as described with reference FIG. 9. Similarly, the mask threshold value (Q) can be a threshold value that is determined programmatically, a threshold value that is provided by a practitioner, and/or a predetermined threshold value.

At operations 506 and 508, indices x and y are set to a first x-y location (e.g., x=1 and y=1) to be processed in a certain RAP map. At operation 510, a time-frame index is set to a certain RAP (e.g., t=1 for first RAP) out of N-number of time frames (e.g., N=15 for fifteen time frames associated with fifteen RAPs). An array Rxy 539 is defined to include N-number of elements for an x-y location across N-number of RAPs (e.g., 534, 536, . . . , and 538 across N-number of RAPs 222, 224, . . . , and 226 for a certain x, y location). Moreover, a mask array P 545 is defined and includes N-number of elements that are associated with the respective elements of the array Rxy 539.

Thereafter, at operation 511 a determination is made as to whether a selected array element Rxy[t] of the array Rxy is greater than or equal to the mask value (Q) (Rxy[t]>=Q). If it is determined at operation 511 that the selected array element is greater than or equal to the mask value (Q), the method 570 continues at operation 513 where the associated array element P[t] in the mask array P 545 is set to the rotational intensity indicated by the mask value (Q) (e.g., Rxy[5]=96). However, if it is determined at operation 511 that the selected array element Rxy[t] of the array Rxy 539 is not greater than or equal to the mask value (Q), the method 570 continues at operation 515 where the associated array element P[t] of the mask array P 545 is set to the rotational intensity value of zero (0).

A determination is made at operation 514 as to whether there are more time-frames to process (e.g., is time frame t<N-number of time frames). If it is determined at operation 514 that there are more time frames to process, the method 500 continues at operation 516, where t is incremented to the next time frame (e.g., t+1). Operations 511-516 are performed to process successive time frames t, setting successive array elements of the array P[t] to rotational intensity value (Q) or zero (0) across the N-number of RAPs.

However, if it is determined at operation 514 that there are no more time frames to process, the method 500 continues at operation 519 to define an array M 547, which includes largest L-number of intensity values as masked according to (Q) from the N-intensity values in the P array 545. For example, for filter level L=3 and Q=96, M array 547 is defined to include the largest three (3) intensity values as masked by Q out of the fifteen intensity values in the P array 545 (e.g., intensity values 96, 96, and 96 associated with certain x-y location across N-number of RAPs 222, 224, . . . , and 226). At operation 520, an intensity value V is set to the smallest intensity value 544c out of the intensity values as masked according to (Q) included in the M array 547 (e.g., value V=96 for certain x-y location across N-number of RAPs 222, 224, . . . , and 226). Thereafter, at operation 521 the aggregated stability map 228c for the filter level L=3 and mask threshold value Q=96 is generated by setting location (x, y) 546c in the aggregated stability map S[L] 228c to value V (e.g., value for location (x, y) 546c is set to 96).

At operation, 522, a determination is made as to whether there are more rows to process. If it is determined at operation 522 that there are more rows to process, index x is incremented (e.g., x+1) at operation 524, and the method 570 continues again at operation 510. Operations 510-522 are performed to process an x-y intensity value as masked for all rows of across the N-number of RAPs. However, if it is determined at operation 522 that there are no more rows to process, the method 570 continues at operation 526, where a determination is made as to whether there are more columns to process. If it is determined at operation 526 that there are more columns to process, index y is incremented (e.g., y+1) at operation 528, and the method 570 continues again at operation 508. Operations 508-526 are performed to process an x-y intensity value as masked for all columns across the N-number of RAPs.

However, if it is determined at operation 526 that there are no more columns to process, the method 570 continues at operation 530, where a completed aggregated stability map S[L] 228c is saved. For example, the aggregated stability map S[L] 228c can be saved to the analysis database 118. It should be noted that the example method 570 sets 29×32 x-y locations in the aggregated stability map based on filter level (L) as masked by mask value (Q), in accordance with the description provided hereinabove.

Figure 6:
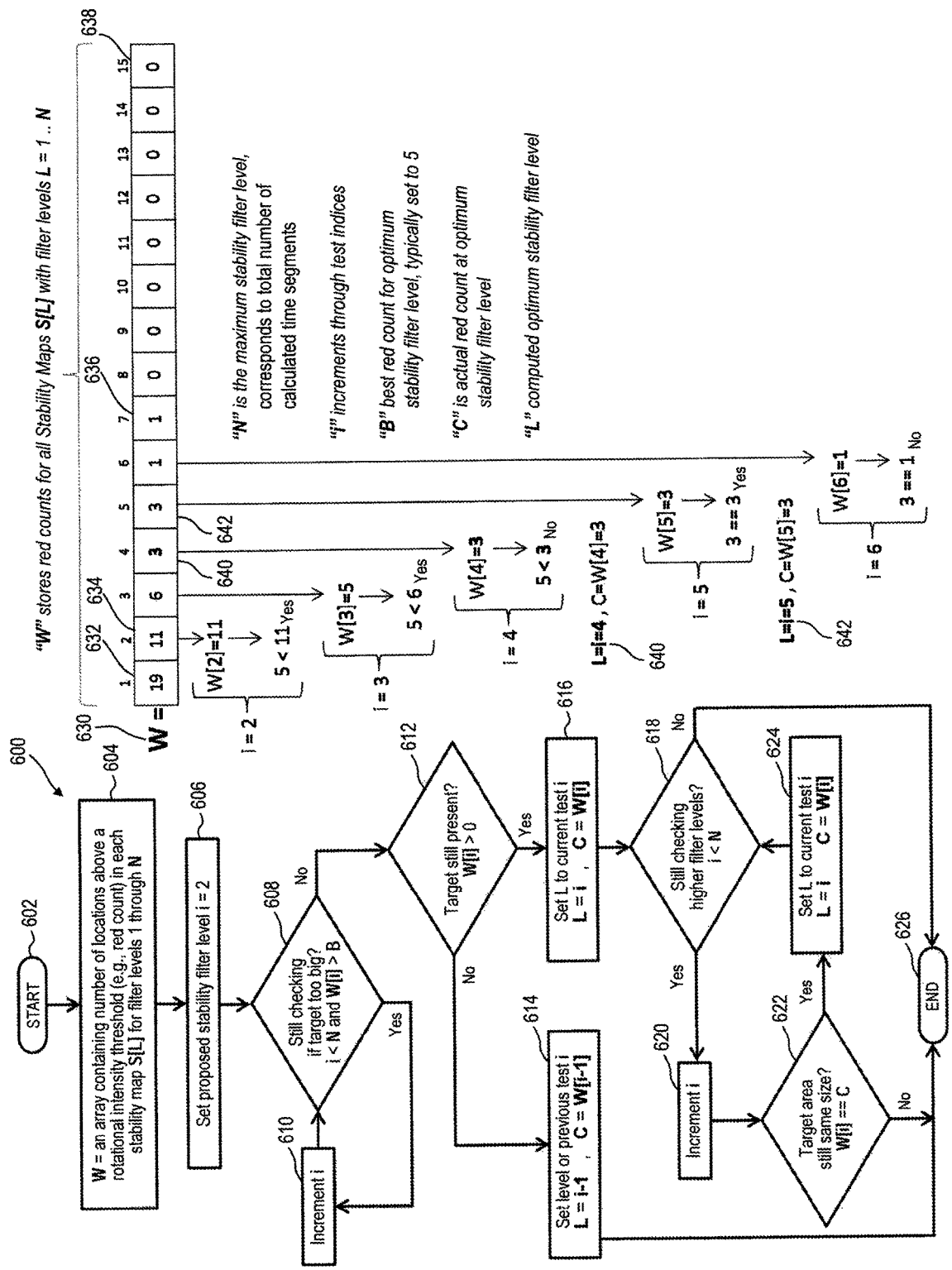
FIG. 6 illustrates a flowchart of an example method of programmatically determining an initial filter level for an aggregated stability map.

FIG. 6 is a flowchart of an example method 600 of programmatically determining an initial filter level (L) for an aggregated stability map.

The method 600 starts at operation 602, which initially generates a plurality of aggregated stability maps for different filter levels from the rotational area profile (RAP) maps or RAPs (e.g., filter levels 1 to N (e.g., 15 analysis intervals or time frames)) using, for example, method 500 of FIG. 5A for each of the filter levels. These aggregated stability maps S[L] for the different filter levels L=1 to N (e.g., S[1], S[2], . . . , and S[N]) can be stored in the analysis database 118. In the alternative, RAPs for programmatically determining the initial filter level (L) can also be determined using method 550 in FIG. 5B for each of the filter levels.

At operation 602, an array (W) 630 is generated that includes at each element a number of x-y locations that have intensity values above a predetermined rotational intensity threshold (e.g., red count) in each aggregated stability map at a different filter level (e.g., filter levels 1-N). For example, the predetermined rotational intensity threshold can be set to a value of 80 on a color scale. Higher and lower values can similarly be used for the predetermined rotational intensity threshold, such as a value of 75, 85, 90, or 95, and so on. According to the foregoing example, any rotational intensity threshold that is greater than the rotational intensity threshold (e.g., 80 in this example) will be counted as part of a total number of x-y locations above the predetermined rotational intensity threshold. Similarly, a greyscale value can be defined to represent the predetermined rotational intensity threshold.

As illustrated in the example array W 630, element 632 (e.g., associated with the aggregated stability map S[1]) includes nineteen (19) x-y locations that are above the predetermined rotational intensity threshold (e.g., "red count"). As further illustrated in array W 630, element 634 (e.g., associated with the aggregated stability map S[2]) includes a decreasing red count number of eleven (11) x-y locations above the predetermined rotational intensity threshold. Similarly, element 636 (e.g., associated with the aggregated stability map S[7]) includes a red count number of one (1) x-y location above the predetermined rotational intensity threshold, which is the last element in W array 630 that has a red count value above the predetermined rotational intensity threshold. The remaining red count values are zero (0) for elements in W array 630 between element 636 and the last element 638.

At operation 606, an index (i) is set to a value two (2), an initially proposed stability filter level for an aggregated stability map. While a value of one (1) can be used for the initially proposed stability filter level, the aggregation of RAP maps into an aggregated stability map with filter level of one (1) according to method 600 will produce an aggregated stability map having at each x-y location the highest rotational intensity that is determined among the plurality of RAP maps. More specifically, the aggregated stability map will show the highest intensity value at each x-y location across the plurality of RAP maps, e.g., filter level of one (1) is the most inclusive filter level so that a rotational intensity of an x-y location that appears only once across the RAPs will be included in the aggregated stability map. By starting at filter level of two (2), consideration for the automated filter level is given to an x-y location having rotational intensities that appear at least twice across the RAPs.

At operation 608, a check is performed as to whether a target is too big. More specifically, a determination is made as to whether element W[i] is larger than an empirically set threshold B (e.g., B=5 is set for an optimum stability filter) and index (i) is less than N (N=15). If it is determined at operation 608 that the red count in element W[i] is greater than threshold of five (5) and the index (i) is less than fifteen (15), the method 600 continues at operation 610, where index (i) is incremented (e.g., i+1). As illustrated in array W 630 at element 640, the method 600 continues to increment (i) until i=4 and the element at W[i]=3.

However, if it is determined at operation 608 that the red count in element W[i] is not greater than threshold of five (5) or the index (i) is not less than fifteen (15), the method 600 continues at operation 612, where a determination is made as to whether the target is still present (e.g., is W[i]>0). As described above, operation 612 is performed when i=4 and the element at W[i]=3, in order to test whether the target W[i] is still present, i.e., greater than a zero (0).

If it is determined at operation 612 that the target is still present, the method 600 continues at operation 616, where the filter level L is set to index (i) (e.g., L=i) and actual red count is set to the current value in array W 630 (e.g., C=W[i]). Based on the foregoing example, L=4 and C=3. At operation 618, a determination is made as to whether the current index (i) is less than fifteen (15) (e.g., i<15), i.e., determine whether there might be a higher filter level (L) that might be used. If it is determined at operation 618 that i<15, the method 600 continues at operation 620, where index (i) is incremented (e.g., i+1). At operation 622, a determination is made as to whether the target area is still the same size (e.g., W[i]==C).

If it is determined at operation 622 that the target is still the same size (e.g., W[i]==C), the method 600 continues at operation 624, wherein the level L is set to the current index (i) and the actual red count is set to the current value in the array W 630 (e.g., C=W[i]). Based on the foregoing example, the fifth element 642 in array W 630 is still three (3) (e.g., W[5]=3). Operations 618-624 are performed while the target area is the same size. If it is determined at operation 622 that the target is not the same size (e.g., W[i]!=C), then method 600 ends at operation 626. For example, the sixth element in array W 630 is one (1) (e.g., W[6]=1).

However, if it is determined at operation 612 that the target is not present, the filter level L is set to the previous index (e.g., L=i-1) and the actual red count is set to the previous value in array W 630 (e.g., C=W[i-1]). This can occur if for a certain iteration of (i) W[i]>5 and on the next iteration W[i+1]=0. In this case, the method 600 uses the previous index (i-1) and W[i-1]. Thereafter, the method 600 ends at operation 626.

Figure 7:
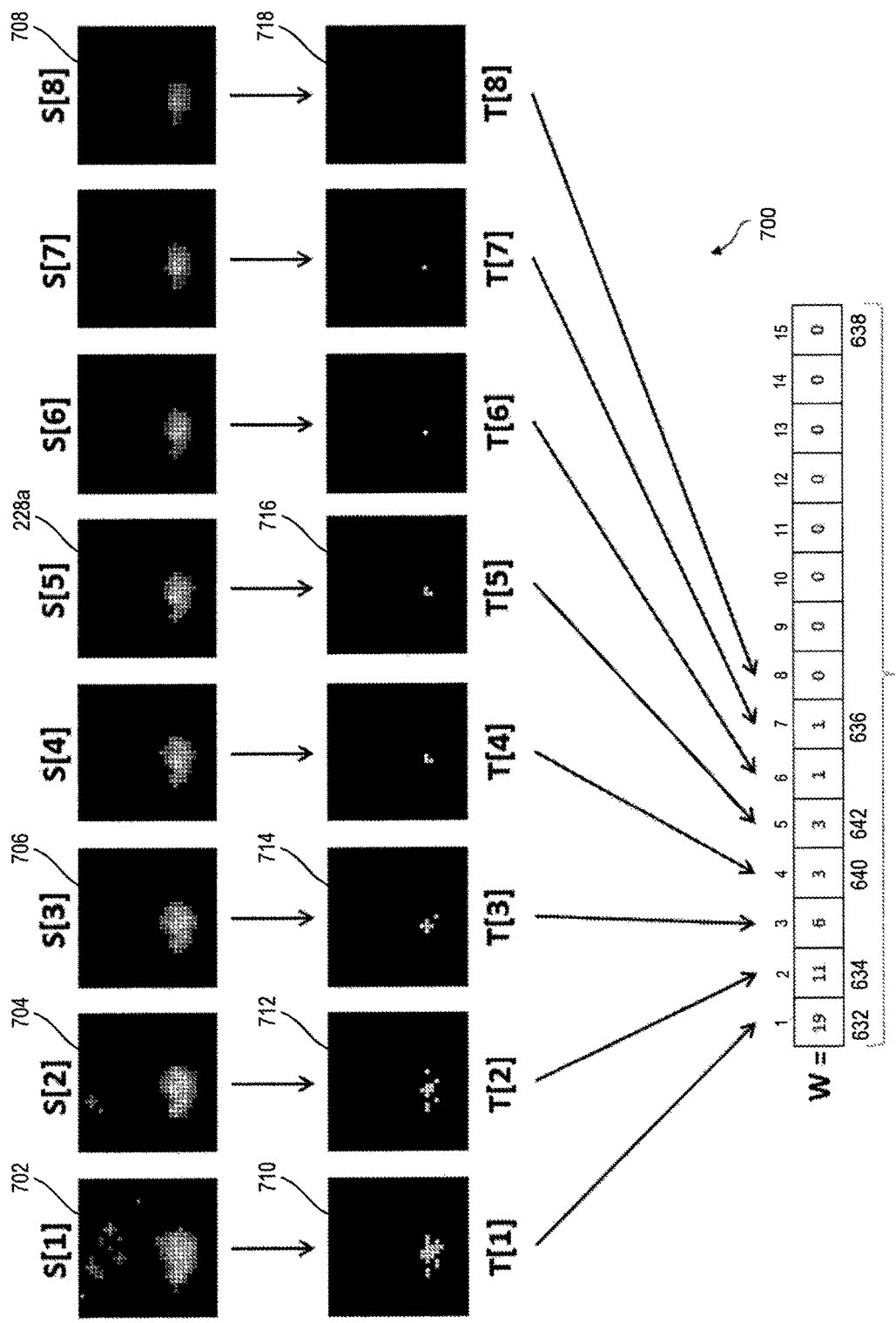
FIG. 7 illustrates an example block diagram of aggregated stability maps for different filter levels with associated x-y locations that have intensity values above a predetermined rotational intensity threshold.

FIG. 7 is an example block diagram 700 that illustrates the aggregated stability maps S[L] 702, 704, 706, 228a, . . . , and 708 for different filter levels L, only through filter level eight (8) which does not have any x-y locations that have an intensity value above the predetermined rotational intensity threshold (e.g., red count).

For the sake of clarity, aggregated stability maps S(L), generated in accordance with method 500 of FIG. 5A, were thresholded into threshold maps T[L] 710, 712, 714, 716, . . . , and 718 according to respective intensity values above the threshold intensity value at x-y locations. It is noted that aggregated stability maps S[9]-S[15] and respective threshold maps T[9]-T[15] are not shown because they contain no x-y locations above the threshold intensity value. The aggregated stability maps S(L) can similarly be generated in accordance with method 550 of FIG. 5B.

Figure 8:
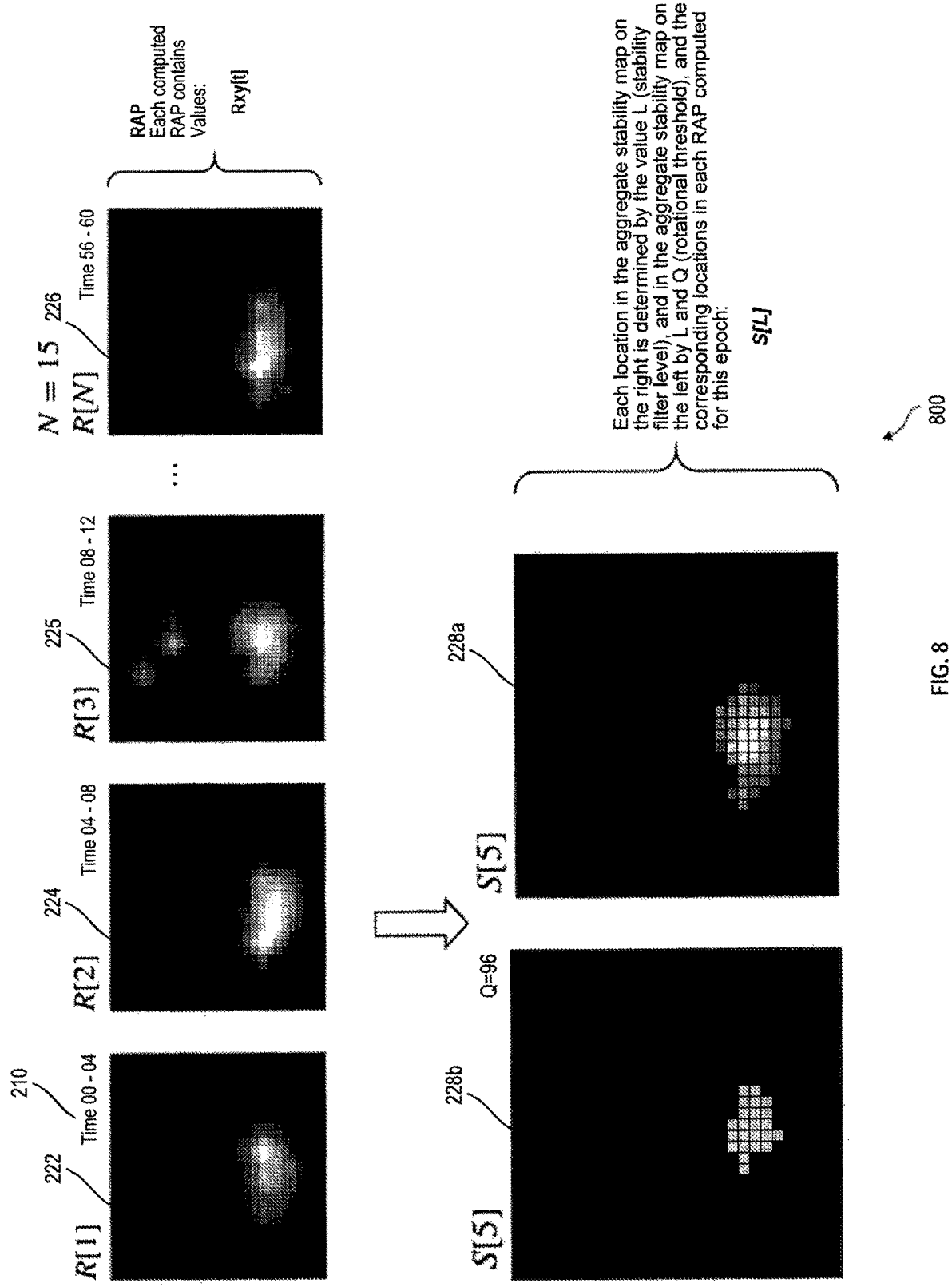
FIG. 8 illustrates an example block diagram of example RAP maps amalgamated into an aggregated stability map for a programmatically determined filter level.

FIG. 8 is an example block diagram 800 that illustrates example rotational area profile (RAP) maps 222, 224, 225, . . . , 226 for N=15 based on the block diagram 200 illustrated in FIG. 2, amalgamated into an aggregated stability map 228a and/or aggregated stability map 228b. As illustrated in the aggregated stability map 228a and/or aggregated stability map 228b, the locations that have rotation intensities values after aggregation form clusters.

Each of the fifteen (15) RAPs 222, 224, 225, . . . , 226 includes 29×32 intensity values Rxy(t) for the different time intervals (t) (t=1-15). The fifteen RAPs are amalgamated into an aggregated stability map S[L] 228a based on filter level L of five (L=5), or an aggregated stability map S[L] 228b based on filter level L of five (L=5) and mask value Q of 96 (Q=96), which aggregated stability map can be programmatically determined according to the methods 500 or 550, and method 600, as illustrated in FIGS. 5A, 5B, and 6, respectively.

It should be noted that each location in the aggregated stability map S[5] 228a is determined by the filter value L=5 and the corresponding locations in each constituent RAP computed for this epoch. It should further be noted that each location in the aggregated stability map S[5] 228b is determined by the filter value L=5 and the corresponding locations in each constituent RAP computed for this epoch, as thresholded by mask value Q=96. The aggregated stability map 228b can help to provide better contrast continuity of rotational intensity values for the different x-y locations of RAPs 222, 224, 225, . . . , 226.

FIG. 9 is an example graphical user interface (GUI) 900 generated in accordance with FIGS. 1-8. More specifically, GUI 900 includes an epoch timeline adjustment tool 902, an animated activation movie with RAP 912, a stability filter adjustment tool 914, and one or more aggregated stability maps, such as an aggregated stability map 228a and/or aggregated stability map 228b.

The epoch timeline adjustment tool 902 includes analysis intervals 204. The analysis intervals 204 include fifteen (15) even intervals 206 (e.g., 0-4, 4-8, 8-12, . . . , and 56-60) and also fourteen (14) odd intervals 208 (e.g., 2-6, 6-10, 10-14, . . . , and 54-58). As an example, a total of twenty-nine (29) analysis intervals can be defined for the 60-second epoch of signal data. The movie selector 904 can be adjusted by the practitioner to any computed analysis intervals 204 with acceptable signal quality (sq) used for computations that are indicated a mark "+" on a white background. In contrast, computed analysis intervals 204 that do not have acceptable signal quality (sq) are indicated with a mark "–" and cannot be selected.

More specifically, as illustrated in the epoch timeline 902, the following even intervals can be selected: 0-4, 4-8, . . . , 36-40, 52-56, and 56-60. Additionally, as illustrated in the epoch timeline 902, the following odd intervals can be selected: 42-46, 50-54, and 54-58. Accordingly, a total of fifteen (15) selectable intervals of time can be selected in association with the 60-second epoch of signal data. It is noted that more or fewer selectable time intervals of time can be defined, as well as more or fewer time intervals can be selected. Selectable time interval 28-32 is the best signal quality among the fifteen (15) selectable time intervals, as indicated by a rectangular shape with a hatched pattern 906.

The fifteen (15) selectable analysis intervals are used for the generation of the animated activation movies, associated RAPs, and the aggregated stability map 228a and/or aggregated stability map 228b. For example, animated activation movie illustrated in GUI 900 is for selectable interval of time 16-20 seconds of the 60 second epoch of signal data. The RAP 910 is generated based on the animated activation movie 908.

The animated activation movie 908 with overlaid RAP 912 can be presented for the selected interval of time 904. Upon selection of a different selectable interval of time in the epoch timeline 902 using movie selector 904, a different animated activation movie and the associated RAP are retrieved and presented as described above.

The stability filter adjustment tool 914 includes a level selector 916. The level selector 916 can be initially set programmatically to filter level L of five (L=5), as described in the foregoing examples. The mask value Q can be set programmatically, can be entered using a similar mask adjustment tool/intensity selector (not shown), or can be a predetermined value. The aggregated stability map 228a and/or aggregated stability map 228b is generated for the entire epoch (e.g., 60 seconds of signal data). More specifically, the aggregated stability map 228a and/or aggregated stability map 228b is an amalgamation of the RAPs for the fifteen selectable analysis intervals at a selected filter level over the entire epoch of signal data.

The practitioner can adjust the level selector 916 to a higher or lower level. Upon selection of a different stability filter level using level selector 916, an aggregated stability map for a different level can be retrieved and presented (e.g., aggregated stability map S[L] based on the selected filter level (L) and the corresponding x-y locations in each of the fifteen selectable RAPs). Similarly, the practitioner can adjust mask value of the aggregated stability map S[L] to a higher or lower mask value for a given filter level (L). Upon such adjustment, the x-y locations in the stability map S[L] 228b having previous mask values can be adjusted to the newly selected mask values and then re-displayed.

In some cases, the stability filter adjustment tool 914 with its level selector 916 can be omitted. If so, the values of the corresponding x-y location in the fifteen (15) selectable RAPs can be automatically averaged to generate a value for an associated x-y location of an aggregated stability map, which in this case is thus not based on a filter level (L).

FIG. 10 is a block diagram 1000 of an aggregated stability map generated based on an adjusted filter level (L) from RAP maps as described in connection with FIG. 5A. In this example, L is equals to three (L=3).

The adjusted filter level (L) can be similarly determined programmatically or provided by a practitioner using stability level selector 916 of the stability filter adjustment tool 914.

As illustrated in block diagram 1000, level three (3) 1001 is determined programmatically or provided using stability level selector 916. An array P 1002 is defined to include N-number of elements for an x-y location across N-number of RAPs (e.g., 534, 536, . . . , and 538 across N-number of RAPs 222, 224, . . . , and 226 for a certain (x, y) location).

More specifically, the array P 1002 includes intensity values for the same x-y location from different RAPs 222, 224, . . . , and 226.

An array M 1004 is defined to include largest L-number of intensity values from the N-intensity values in the P array 1002. For example, for filter level L=3, M array 1004 is defined to include the largest three (3) intensity values out of the fifteen intensity values in the P array 1002 (e.g., intensity values 97, 99, and 97 for certain x-y location across N-number of RAPs 222, 224, . . . , and 226). The intensity value V is set to the smallest intensity 1005 value out of the intensity values included in the M array (e.g., value V=97 for certain x-y location across N-number of RAPs 222, 224, . . . , and 226). The aggregated stability map for the filter level L=3 is generated by setting location (x, y) 1006 in the aggregated stability map S[L] 1008 to the intensity value V (e.g., value for location (x, y) 1006 is set to 97).

It is noted that all rows x and columns y are processed in a similar fashion to set appropriate intensity values V for each of the locations (x, y) based on the filter level L=3 across the RAPs. The aggregated stability map S[L] 1008 can be saved to the analysis database 118 for later retrieval and presentation. It should be noted that 29×32 x-y locations are set in the aggregated stability map based on filter level L=3, in accordance with the description as provided hereinabove. Moreover, other aggregated stability maps based on different filter levels are generated in a similar fashion.

Figure 11:
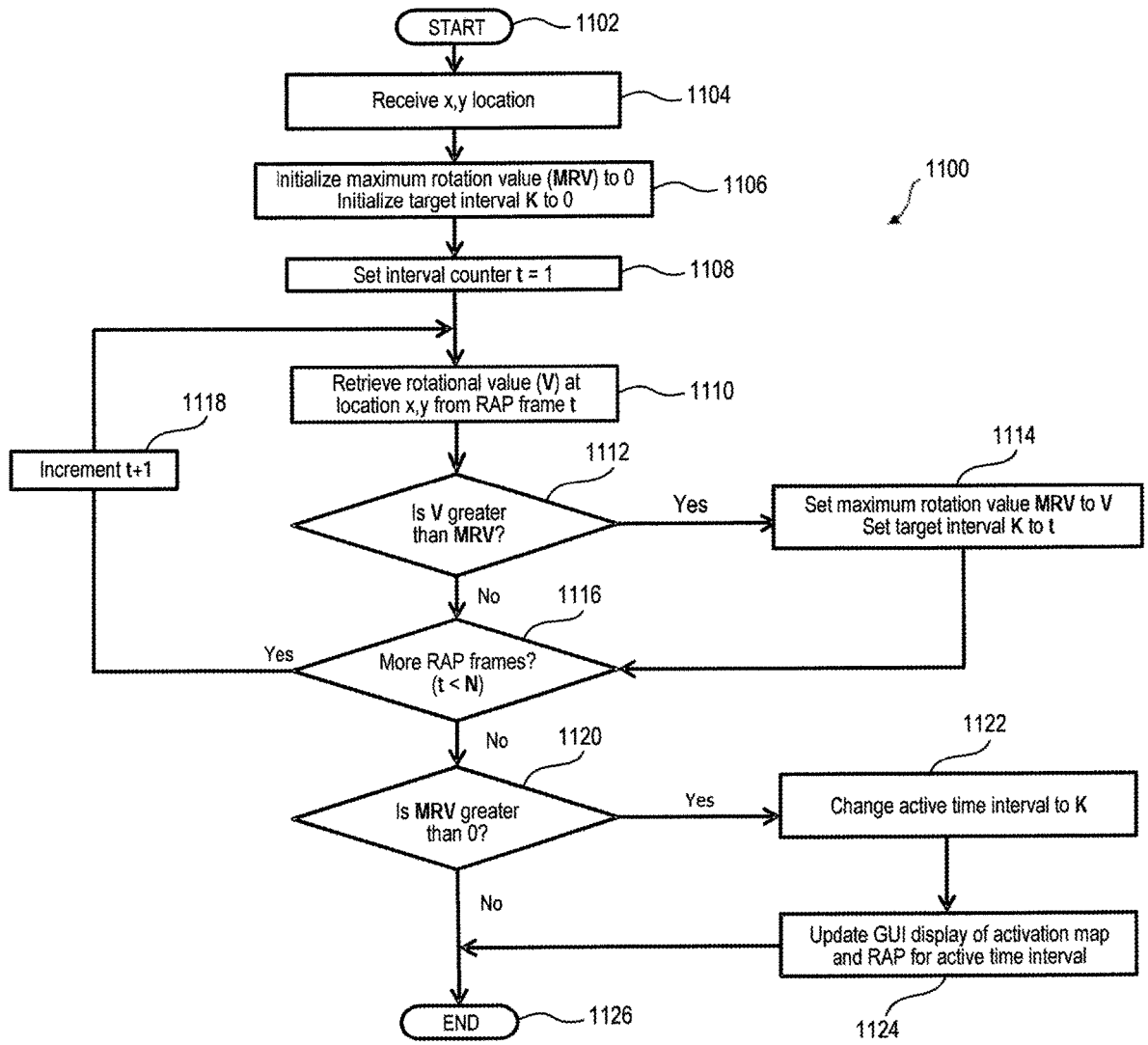
FIG. 11 illustrates a flowchart of an example method of determining an analysis interval and an associated RAP map based on a location of the aggregated stability map.

FIG. 11 is a flowchart of an example method 1100 of determining an analysis interval and an associated RAP map based on a location of the aggregated stability map.

The method 1100 starts at operation 1102. At operation 1104, an x-y location is received. For example, an x-y location can received when a practitioner clicks on a location in an aggregated stability map, e.g., aggregated stability map 228a or aggregated stability map 228b as illustrated in FIG. 9.

At operation 1106, a maximum rotation value (MRV) is initialized to zero (0) and the target analysis interval K is initialized to zero (0). At operation 1108, the analysis interval index t is set to one (1) (e.g., t=1).

Thereafter, at operation 1110 a rotational value (V) is retrieved from the x-y location of a RAP map for the time interval t. At operation 1112, a determination is made as to whether the rotational value V is greater than the maximum rotational value MRV. If it is determined at operation 1112 that V is greater than MRV, the method 1100 continues at operation 1114, where the maximum rotational value MRV is set to V and the target analysis interval K is set to t. The method 1100 then continues at operation 1116, as described below. However, if it is determined at operation 1112 that V is not greater than MRV, the method 1100 continues at operation 1116.

At operation 1116, a determination is made as to whether there are more RAP maps to process, e.g., determination is made as to whether time interval t is less than N (e.g., N=15). If it is determined at operation 1116 that t is less than N, then index t is incremented (e.g., t+1) at operation 1118. Operations 1110-1118 are performed to obtain the maximum rotational value MRV at the x-y location of a RAP across the plurality of RAPs and the associated analysis interval, which contributed to the determination of the x-y location in the aggregated stability map.

At operation 1120, a determination is made as to whether the maximum rotational value MRV is greater than zero (0). If it is determined at operation 1120 that MRV is greater than zero (0), the method 1110 continues at operation 1122, where an active analysis interval is set to the target analysis interval K. At operation 1124, the animated activation movie and associated RAP map are retrieved and presented for the active analysis interval. The method 1110 then ends at operation 1126.

However, if it is determined at operation 1120 that MRV is not greater than zero (0), the method ends at operation 1126.

The foregoing method 1100 retrieves the animated activation movie and associated RAP map for the active analysis interval based on a highest rotation intensity value at a certain x-y location across the RAPs, which provides best representation and/or illustration associated with that x-y location in order to assist the practitioner.

However, it should be noted that the method 1100 can be modified to retrieve the animated activation movie and associated RAP map for an active analysis interval based on a lowest rotation intensity value at a certain x-y location across the highest L-number rotation intensity values, which rotation intensity value was used to populate the aggregated stability map. Similarly, method 1100 can also be modified to retrieve the animated activation movies and associated RAP maps for the analysis intervals based on the highest L-number rotation intensity values that contributed to the aggregated stability map.

Figure 12:
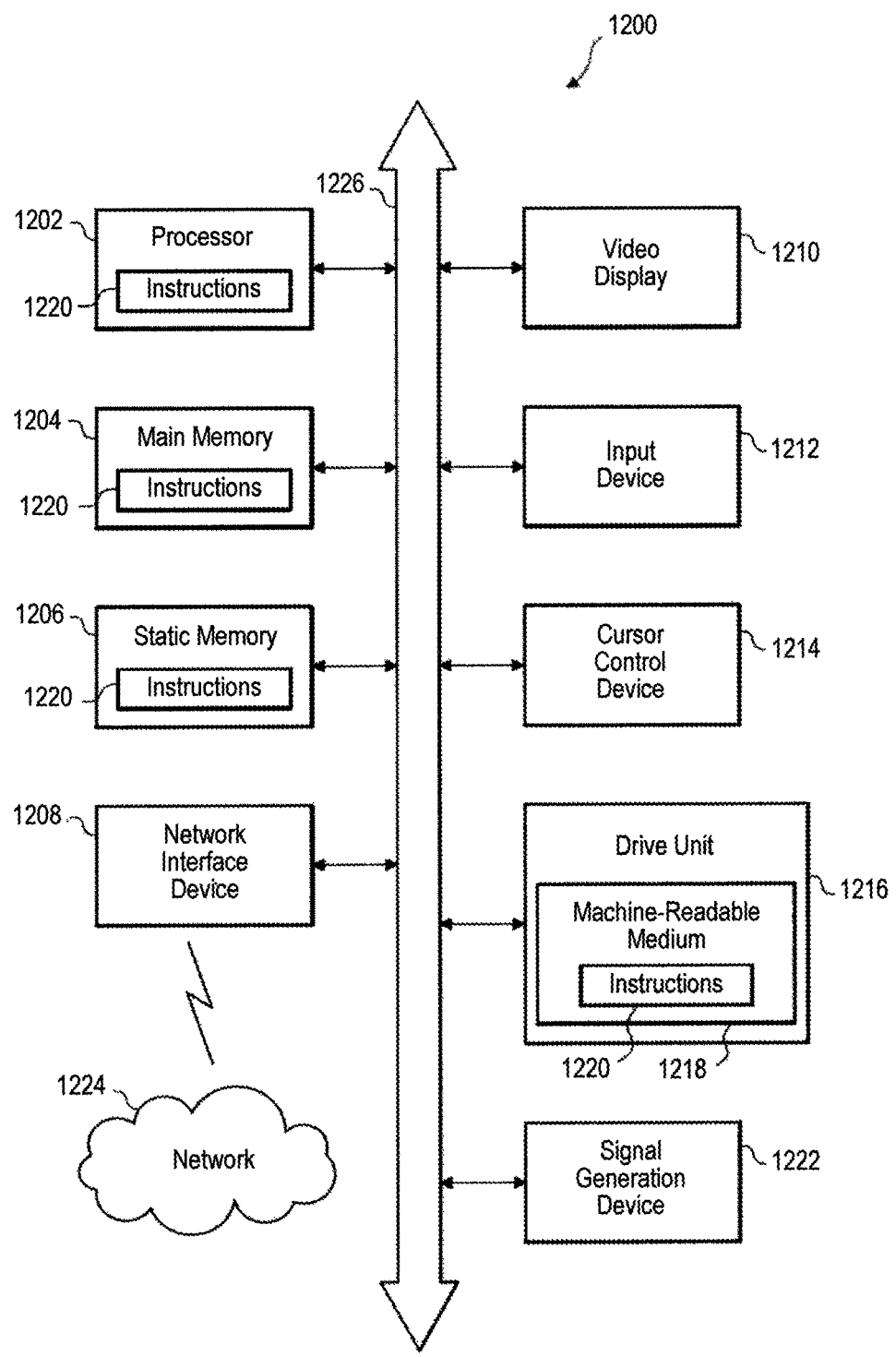
FIG. 12 illustrates a block diagram of an illustrative embodiment of a general computer system.

FIG. 12 is a block diagram of an illustrative embodiment of a general computer system 1200. The computer system 1200 can include a set of instructions that can be executed to cause the computer system 1200 to perform any one or more of the methods or computer based functions disclosed herein in FIGS. 1-11. The computer system 1200, or any portion thereof, can operate as a standalone device or can be connected, e.g., using a network or other connection, to other computer systems or peripheral devices. For example, the computer system 1200 can be the computing device 116 that defines an aggregated stability map of a rotational source over a plurality of time intervals, and can further be connected to other systems and devices, such as signal processing device 114 and analysis database 118, via a network.

The computer system 1200 may also be implemented as, or incorporated into various devices, such as a personal computer (PC), a tablet PC, a personal digital assistant (PDA), a mobile device (e.g., smartphone), a palmtop computer, a laptop computer, a desktop computer, a communications device, a control system, a web appliance, or any other machine capable of executing a set of instructions (sequentially or otherwise) that specify actions to be taken by that machine. Further, while a single computer system 1200 is illustrated, the term "system" shall also be taken to include any collection of systems or sub-systems that individually or jointly execute a set, or multiple sets, of instructions to perform one or more computer functions.

As illustrated in FIG. 12, the computer system 1200 can include a processor 1202, e.g., a central processing unit (CPU), a graphics-processing unit (GPU), or both. Moreover, the computer system 1200 can include a main memory 1204 and a static memory 1206 that can communicate with each other via a bus 1226. As shown, the computer system 1200 can further include a video display unit 1210, such as a liquid crystal display (LCD), an organic light emitting diode (OLED), a flat panel display, a solid state display, or a cathode ray tube (CRT). Additionally, the computer system 1200 can include an input device 1212, such as a keyboard, and a cursor control device 1214, such as a mouse. The computer system 1200 can also include a disk drive (or solid state) unit 1216, a signal generation device 1222, such as a speaker or remote control, and a network interface device 1208.

In a particular embodiment or aspect, as depicted in FIG. 12, the disk drive (or solid state) unit 1216 can include a computer-readable medium 1218 in which one or more sets of instructions 1220, e.g., software, can be embedded. Further, the instructions 1220 can embody one or more of the methods or logic as described herein. In a particular embodiment or aspect, the instructions 1220 may reside completely, or at least partially, within the main memory 1204, the static memory 1206, and/or within the processor 1202 during execution by the computer system 1200. The main memory 1204 and the processor 1202 also can include computer-readable media.

In an alternative embodiment or aspect, dedicated hardware implementations, such as application specific integrated circuits, programmable logic arrays and other hardware devices, can be constructed to implement one or more of the methods described herein. Applications that can include the apparatus and systems of various embodiments or aspects can broadly include a variety of electronic and computer systems. One or more embodiments or aspects described herein can implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an example, non-limited embodiment or aspect, implementations can include distributed processing, component/object distributed processing, and parallel processing. Alternatively, virtual computer system processing can be constructed to implement one or more of the methods or functionality as described herein.

It is also contemplated that a computer-readable medium includes instructions 1220 or receives and executes instructions 1220 responsive to a propagated signal, so that a device connected to a network 1224 can communicate voice, video, or data over the network 1224. Further, the instructions 1220 can be transmitted or received over the network 1224 via the network interface device 1208.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives can be considered a distribution medium that is equivalent to a tangible storage medium. Accordingly, any one or more of a computer-readable medium or a distribution medium and other equivalents and successor media, in which data or instructions can be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods can optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software can also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein can be stored, are included herein.

Thus, a system and method to define an aggregated stability map of a rotational source over a plurality of time intervals associated with a biological rhythm disorder have been described. Although specific example embodiments or aspects have been described, it will be evident that various modifications and changes can be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter can be practiced. The embodiments or aspects illustrated are described in sufficient detail to enable those skilled in the art to practice the teachings disclosed herein. Other embodiments or aspects can be utilized and derived therefrom, such that structural and logical substitutions and changes can be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose can be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 CFR § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A method of generating an aggregated stability map of one or more rotational sources associated with a heart rhythm disorder, the method comprising:
   sensing, using a plurality of sensors, signals associated with the heart rhythm disorder;
   generating, using a processing device, a plurality of rotational area profile maps based on the signals as sensed, each of the rotational area profile maps being for a respective one of a plurality of analysis intervals, each of the rotational area profile maps including rotation intensity values for a plurality of locations associated with rotation of the one or more rotational sources;
   filtering, using the processing device, the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold rotational intensity value;
   generating, using the processing device, an aggregated stability map based on the plurality of rotational area profile maps as filtered, the aggregated stability map including a plurality of locations, each location of the plurality of locations in the aggregated stability map including a rotation intensity value that is based on the highest rotation intensity values as filtered from corresponding locations of the plurality of rotational area profile maps; and
   presenting on a display, using the processing device, the aggregated stability map as generated which amalgamates the rotation intensity values associated with the rotation of the one or more rotational sources over the plurality of analysis intervals, wherein the rotation intensity values of the aggregated stability map help identification of and guidance to the one or more rotational sources in connection with diagnosis or treatment of the heart rhythm disorder.

2. The method of claim 1, wherein automatic determination of the filter number comprises selecting of a highest filter number from a plurality of filter numbers associated with the predetermined number of rotation intensity values in excess of the threshold intensity value.

3. The method of claim 1, further comprising:
   receiving a selection of an analysis interval from the plurality of analysis intervals;
   retrieving an animated activation movie and a rotational area profile map based on the analysis interval, the rotational area profile map being retrieved from the plurality of rotational area profile maps; and
   presenting the animated activation movie and the rotational area profile map overlaid over the animated activation movie.

4. The method of claim 3, further comprising presenting the aggregated stability map as generated in association with the animated activation movie and the rotational area profile map.

5. The method of claim 1, further comprising:
   receiving a location in the aggregated stability map, the location being determined from the plurality of locations in the aggregated stability map; and
   determining an analysis interval related to the location, the analysis interval being determined from the plurality of analysis intervals.

6. The method of claim 5, further comprising:
   retrieving an animated activation movie and a rotational area profile map based on the analysis interval, the rotational area profile map being retrieved from the plurality of rotational area profile maps; and
   presenting the animated activation movie and the rotational area profile map overlaid over the animated activation movie.

7. The method of claim 1, wherein the rotation intensity value of the aggregated stability map is a smallest rotation intensity value out of the filter number of highest rotation intensity values for that location from the corresponding locations of the plurality of rotational area profile maps.

8. The method of claim 1, wherein the rotation intensity value of the aggregated stability map is an average rotation intensity value of the filter number of highest rotation intensity values for that location from the corresponding locations of the plurality of rotational area profile maps.

9. The method of claim 1, further comprising:
   receiving a mask value; and
   generating the aggregated stability map with each location including the rotation intensity value based on the filter number of highest rotation intensity values from the corresponding locations of the plurality of rotational area profile maps, wherein the highest rotation intensity values are masked according to the mask value.

10. The method of claim 1, wherein presenting the aggregated stability map comprises presenting two or more locations of the plurality of locations in the aggregated stability map having a rotation intensity value in excess of the threshold rotational intensity value that form a cluster associated with the diagnosis or treatment of the heart rhythm disorder.

11. A system to generate an aggregated stability map of one or more rotational sources associated with a heart rhythm disorder, the system comprising:

a display;

a plurality of sensors configured to sense signals associated with the heart rhythm disorder;

a processing device; and a memory device storing a plurality of instructions that, when executed by the processing device, cause the processing device to perform operations comprising:

generating a plurality of rotational area profile maps generated based on the signals as sensed, each of the rotational area profile maps being for a respective one of a plurality of analysis intervals, each of the rotational area profile maps including rotation intensity values for a plurality of locations associated with rotation of the one or more rotational sources;

filtering the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold rotational intensity value;

generating an aggregated stability map based on the plurality of rotational area profile maps as filtered, the aggregated stability map including a plurality of locations, each location of the plurality of locations in the aggregated stability map including a rotation intensity value that is based on the highest rotation intensity values as filtered from the corresponding locations of the plurality of rotational area profile maps; and presenting on the display the aggregated stability map as generated which amalgamates the rotation intensity values associated with the rotation of the one or more rotational sources over the plurality of analysis intervals, wherein the rotation intensity values of the aggregated stability map help identification of and guidance to the one or more rotational sources in connection with diagnosis or treatment of the heart rhythm disorder.

12. The system of claim 11, wherein the operations for automatic determination of the filter number comprise selecting a highest filter number from a plurality of filter numbers associated with the predetermined number of rotation intensity values in excess of the threshold intensity value.

13. The system of claim 11, wherein the operations further comprise:

receiving a selection of an analysis interval from the plurality of analysis intervals;

retrieving an animated activation movie and a rotational area profile map based on the analysis interval, the rotational area profile map being retrieved from the plurality of rotational area profile maps; and presenting the animated activation movie and the rotational area profile map overlaid over the animated activation movie.

14. The system of claim 13, wherein the operations further comprise presenting the aggregated stability map as generated in association with the animated activation movie and the rotational area profile map.

15. The system of claim 11, wherein the operations further comprise:

receiving a location in the aggregated stability map, the location being determined from the plurality of locations in the aggregated stability map; and determining an analysis interval related to the location, the analysis interval being determined from the plurality of analysis intervals.

16. The system of claim 15, wherein the operations further comprise:

retrieving an animated activation movie and a rotational area profile map based on the analysis interval, the rotational area profile map being retrieved from the plurality of rotational area profile maps; and presenting the animated activation movie and the rotational area profile map overlaid over the animated activation movie.

17. The system of claim 11, wherein the rotation intensity value of the aggregated stability map is a smallest rotation intensity value out of the filter number of highest rotation intensity values for that location from the corresponding locations of the plurality of rotational area profile maps.

18. The system of claim 11, wherein the rotation intensity value of the aggregated stability map is an average rotation intensity value of the filter number of highest rotation intensity values for that location from the corresponding locations of the plurality of rotational area profile maps.

19. The system of claim 11, wherein the operations further comprise:

receiving a mask value; and generating the aggregated stability map with each location including the rotation intensity value based on the filter number of highest rotation intensity values from the corresponding locations of the plurality of rotational area profile maps, wherein the highest rotation intensity values are masked according to the mask value.

20. The system of claim 11, wherein the operations for presenting the aggregated stability map comprise presenting two or more locations of the plurality of locations in the aggregated stability map having a rotation intensity value in excess of the threshold rotational intensity value that form a cluster associated with treatment of the heart rhythm disorder.

21. A method of treating a heart rhythm disorder, the method comprising:

accessing, using a processing device, a plurality of rotational area profile maps generated based on sensed signals associated with the heart rhythm disorder, each of the rotational area profile maps being for a respective one of a plurality of analysis intervals, each of the rotational area profile maps including rotation intensity values for a plurality of locations associated with rotation of one or more rotational sources;

filtering, using the processing device, the plurality of rotational area profile maps based at least on a filter number of highest rotation intensity values among a total number of rotation intensity values from corresponding locations of the plurality of rotational area profile maps, wherein the filter number is automatically determined from a plurality of filter numbers such that the plurality of rotational area profile maps as filtered includes a predetermined number of rotation intensity values in excess of a threshold rotational intensity value;

generating, using the processing device, an aggregated stability map based on the plurality of rotational area profile maps as filtered, the aggregated stability map including a plurality of locations, each location of the plurality of locations in the aggregated stability map including a rotation intensity value that is based on the highest rotation intensity values as filtered from the corresponding locations of the plurality of rotational area profile maps, wherein the rotation intensity values of the aggregated stability map help identification of and guidance to the one or more rotational sources associated with the heart rhythm disorder; and treating the heart rhythm disorder at a rotational source of the one or more rotational sources based on one or more locations of the plurality of locations in the aggregated stability map having a rotation intensity value in excess of the threshold rotational intensity value.

22. The method of claim 21, further comprising presenting the aggregated stability map as generated which amalgamates the rotation intensity values associated with the rotation of the one or more rotational sources over the plurality of analysis intervals.

23. The method of claim 21, wherein the rotation intensity value of the aggregated stability map is a smallest rotation intensity value out of the filter number of highest rotation intensity values for that location from the corresponding locations of the plurality of rotational area profile maps.

24. The method of claim 21, wherein the rotation intensity value of the aggregated stability map is an average rotation intensity value of the filter number of highest rotation intensity values for that location from the corresponding locations of the plurality of rotational area profile maps.

25. The method of claim 21, further comprising:
receiving a mask value; and
generating the aggregated stability map with each location including the rotation intensity value based on the filter number of highest rotation intensity values from the corresponding locations of the plurality of rotational area profile maps, wherein the highest rotation intensity values are masked according to the mask value.

26. The method of claim 21, wherein treating the heart rhythm disorder at the rotational source is based on two or more locations of the plurality of locations in the aggregated stability map having a rotation intensity value in excess of the threshold rotational intensity value that form a cluster.

* * * * *